United States Patent [19]
Tal et al.

[11] Patent Number: 5,868,785
[45] Date of Patent: *Feb. 9, 1999

[54] HAND-HELD SURGICAL DEVICE AND TOOLS FOR USE THEREWITH, ASSEMBLY AND METHOD

[75] Inventors: Elisha A. Tal, San Francisco; Michael Hogendijk, Sunnyvale; Michael J. Orth, San Jose; Jeffrey J. Christian, San Jose; Jeffrey E. Holmes, San Jose; Robert D. Berkowitz, Menlo Park, all of Calif.

[73] Assignee: Unisurge Holdings, Inc., Charleston, S.C.

[*] Notice: The term of this patent shall not extend beyond the expiration date of Pat. No. 5,433,725.

[21] Appl. No.: 798,373

[22] Filed: Feb. 10, 1997

Related U.S. Application Data

[60] Division of Ser. No. 282,892, Jul. 29, 1994, Pat. No. 5,601,601, which is a continuation-in-part of Ser. No. 806,666, Dec. 13, 1991, Pat. No. 5,433,725.

[51] Int. Cl.$^6$ ..................................................... A61B 17/00
[52] U.S. Cl. ........................... 606/207; 606/174; 606/564
[58] Field of Search .................................. 606/1, 108, 51, 606/52, 170, 174, 205–210; 128/750–755; 604/22; 600/564–567

[56] References Cited

U.S. PATENT DOCUMENTS

| | | |
|---|---|---|
| 3,989,033 | 11/1976 | Halpern et al. . |
| 4,258,716 | 3/1981 | Sutherland . |
| 4,433,687 | 2/1984 | Burke et al. . |
| 4,461,305 | 7/1984 | Cibley . |
| 4,522,206 | 6/1985 | Whipple et al. . |
| 4,674,509 | 6/1987 | Greenberg . |
| 4,881,550 | 11/1989 | Kothe . |
| 4,994,079 | 2/1991 | Genese et al. . |
| 5,286,255 | 2/1994 | Weber . |

*Primary Examiner*—William Lewis
*Attorney, Agent, or Firm*—Flehr Hohbach Test Albritton & Herbert

[57] ABSTRACT

Hand-held surgical assembly for use in performing a laparoscopic medical procedure, comprising a housing. An actuator tube having a bore therein is slidably mounted in the housing. A handle operated mechanism is carried by the housing for causing reciprocatory movement of the actuator tube assembly within the housing.

17 Claims, 14 Drawing Sheets

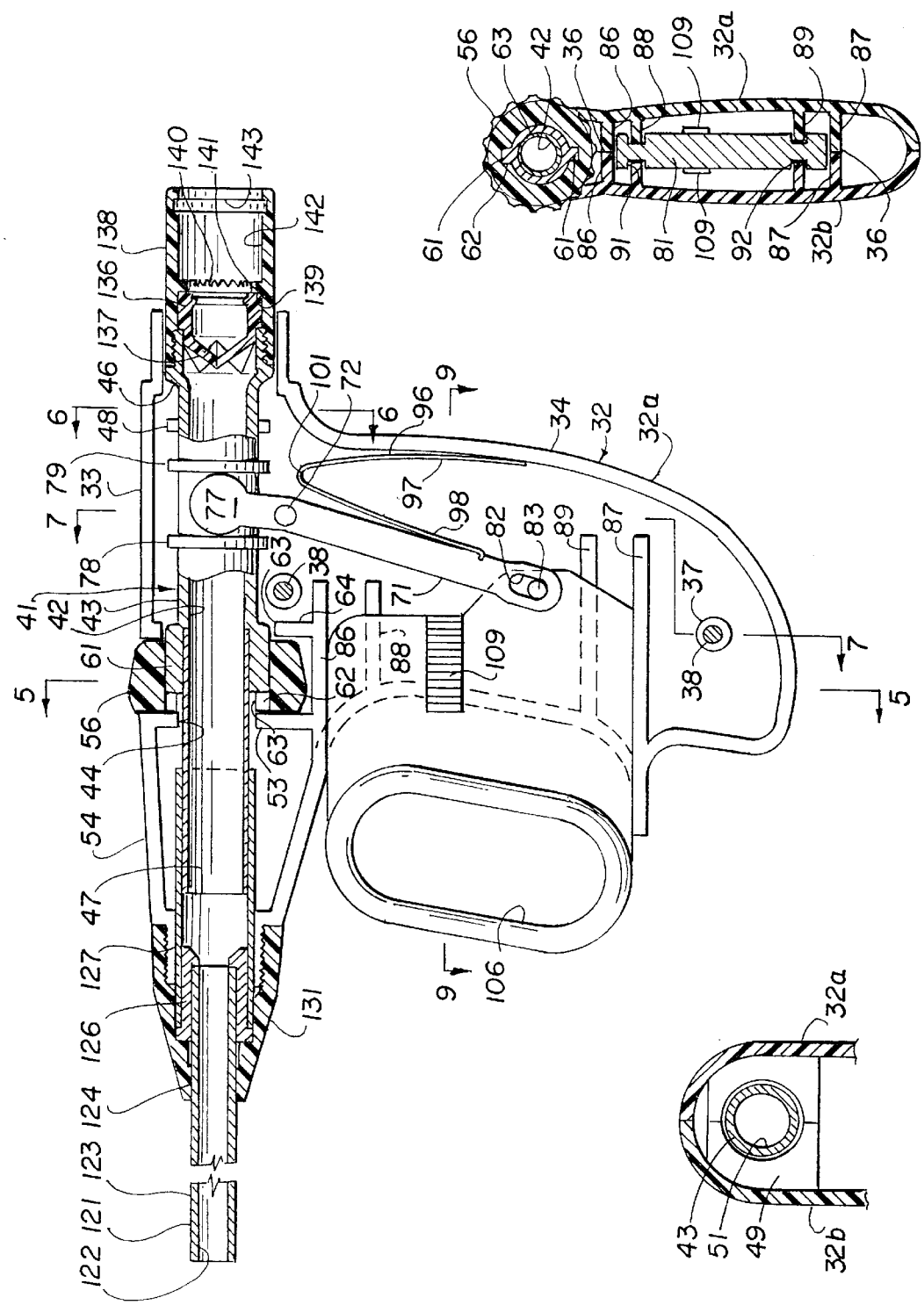

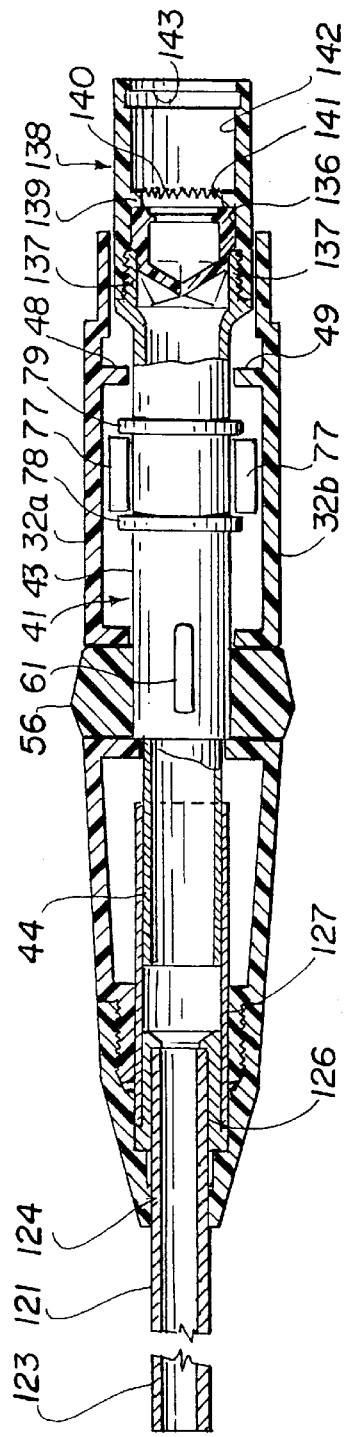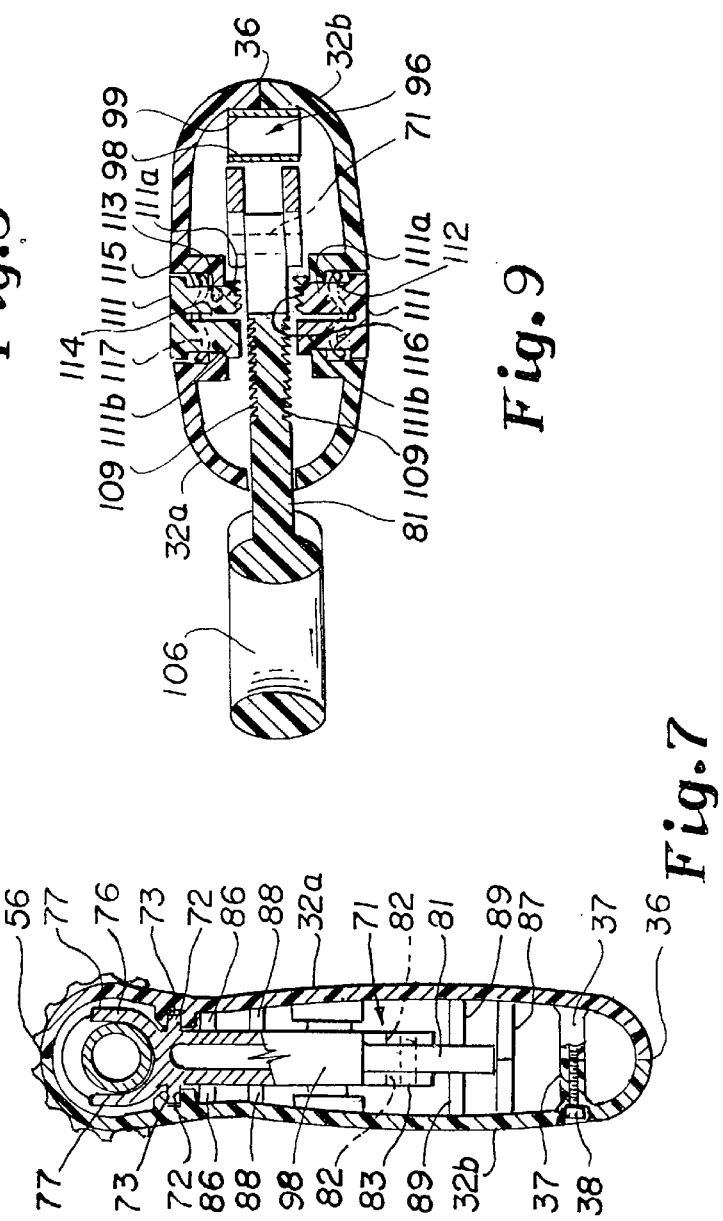

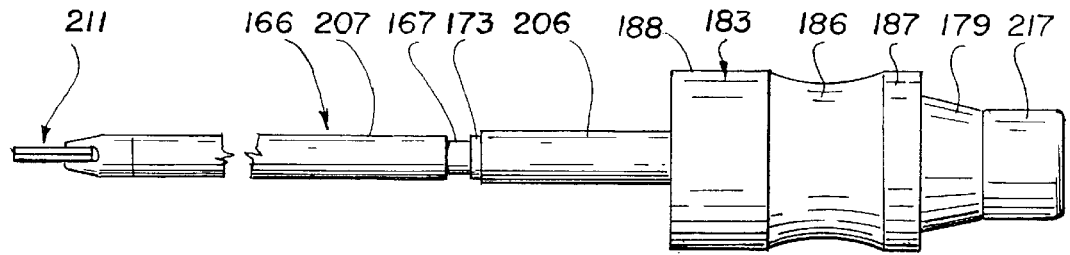
Fig.10
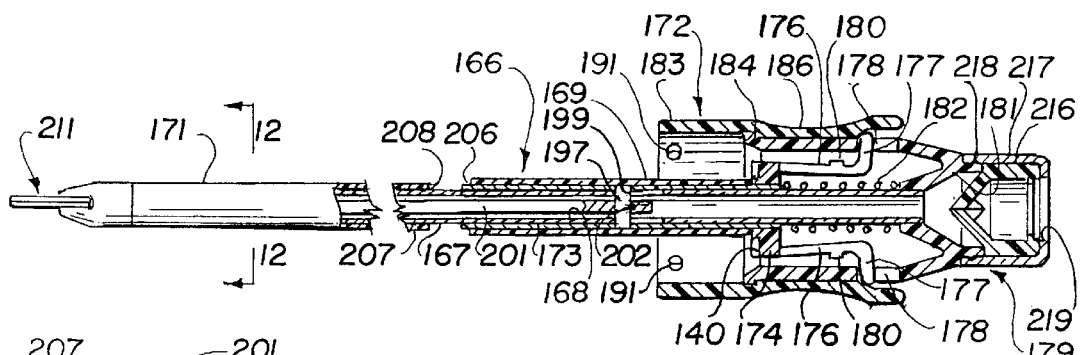
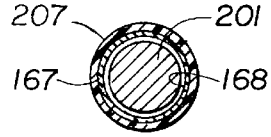
Fig.12
Fig.11
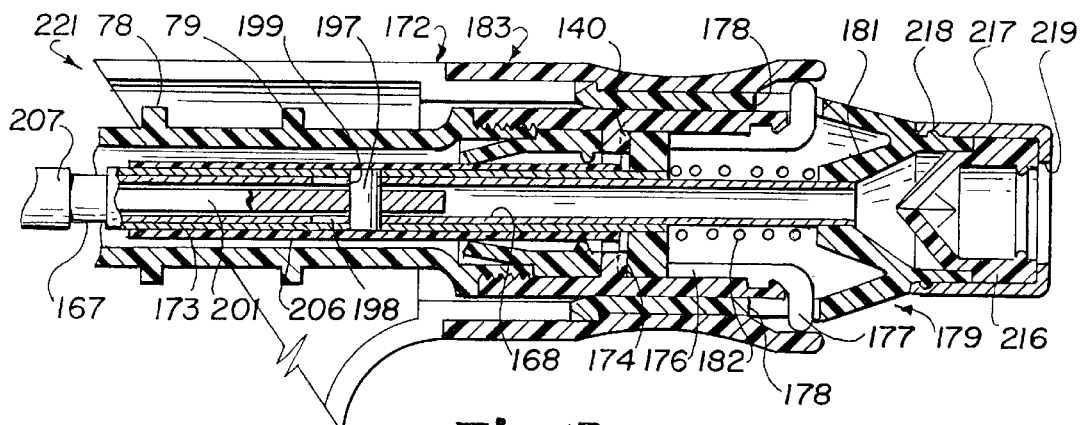
Fig.13

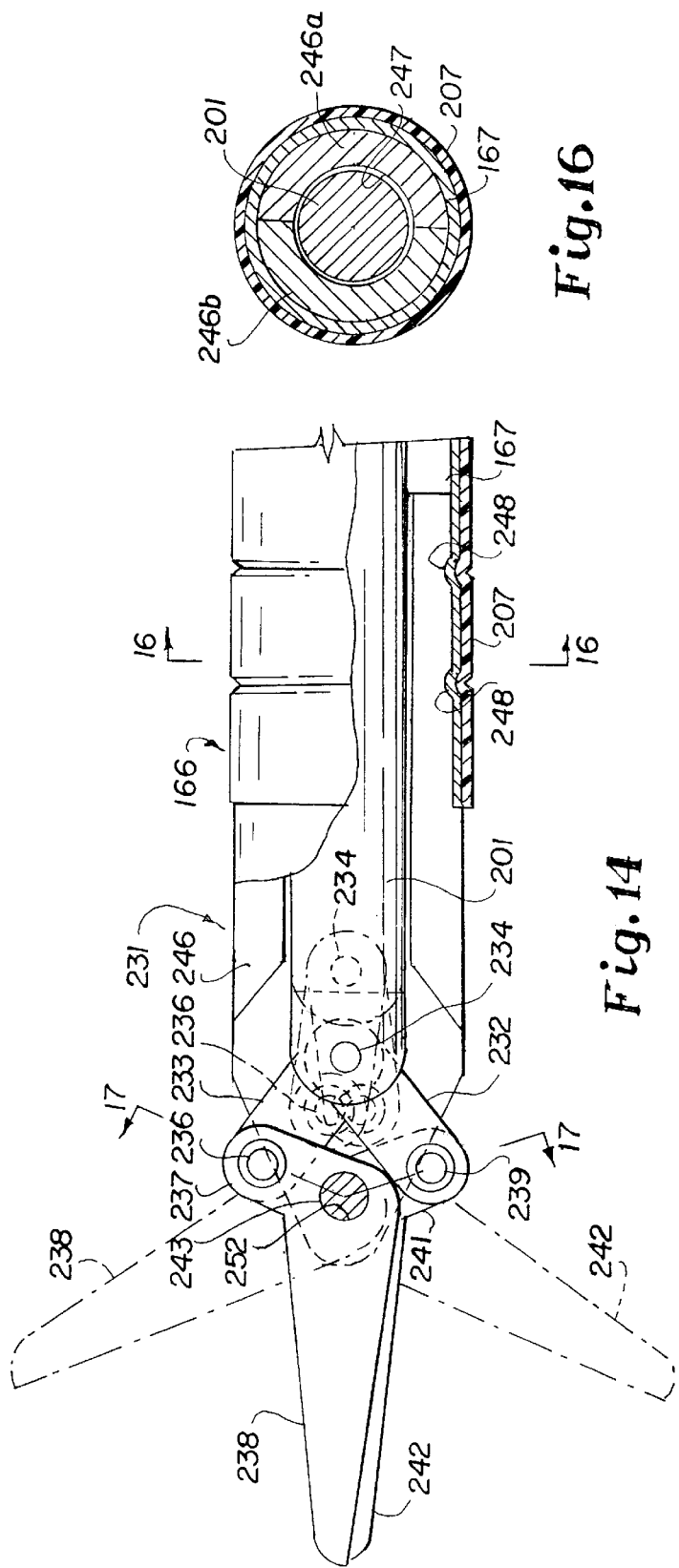

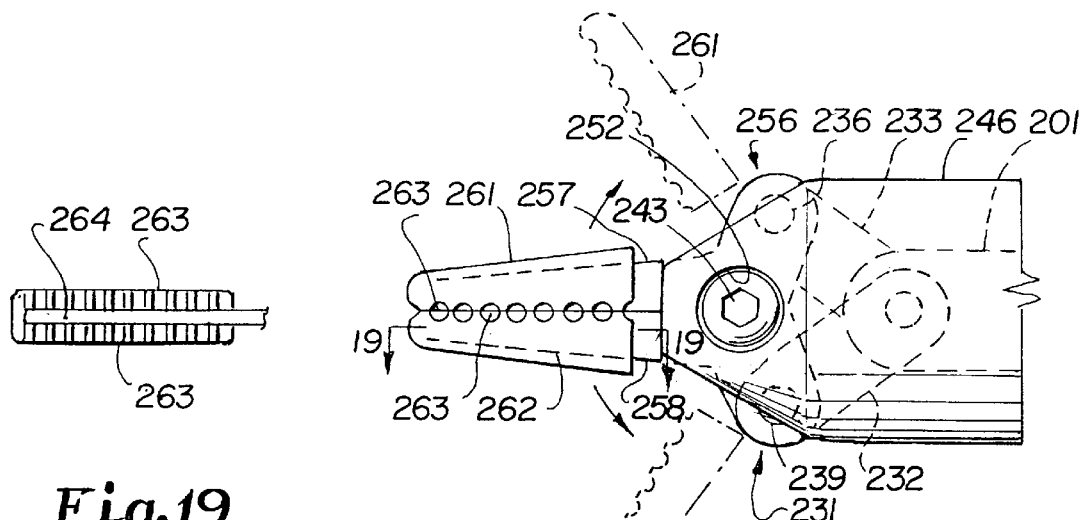
Fig.19
Fig.18
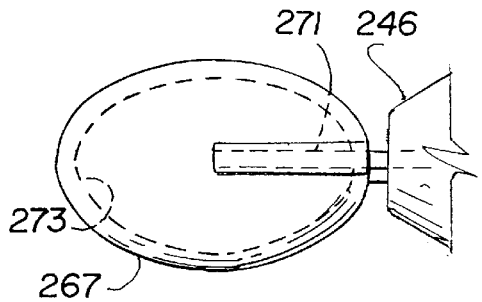
Fig.21
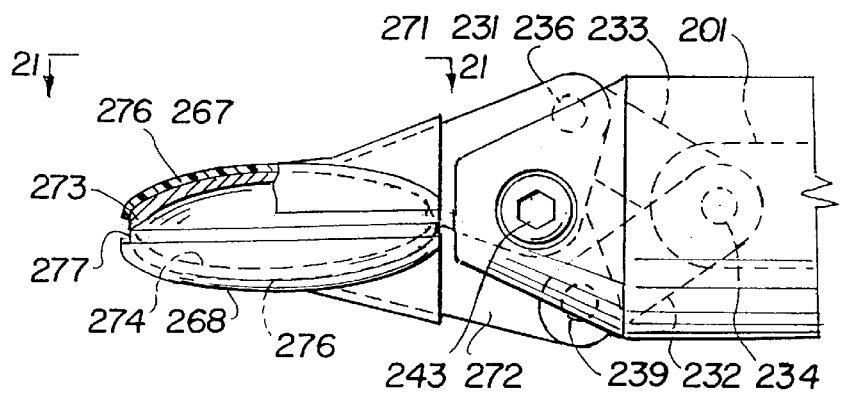
Fig.20

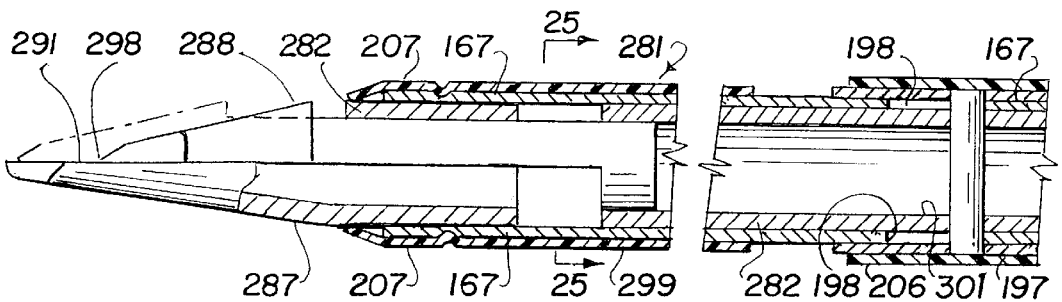
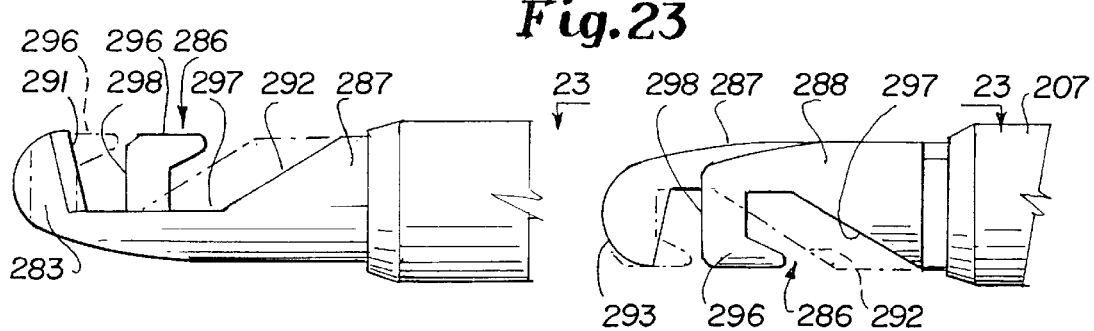
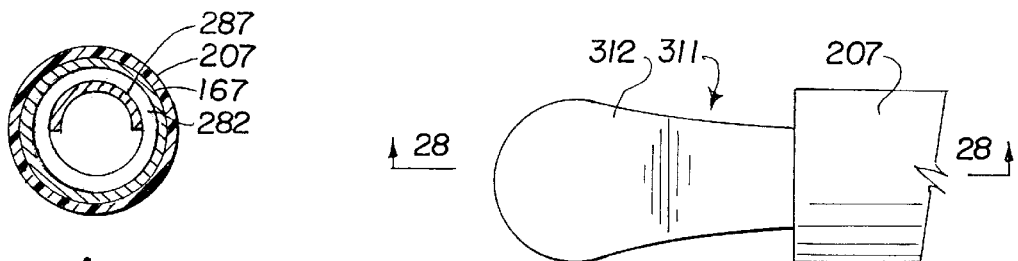
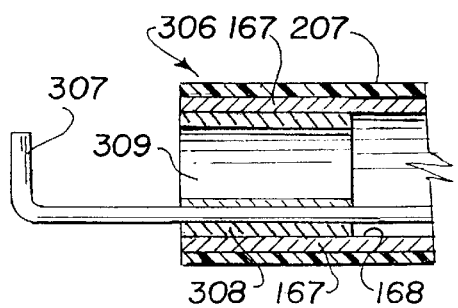
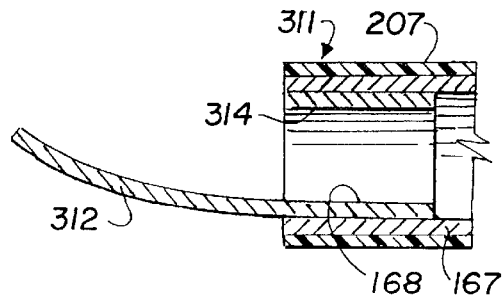

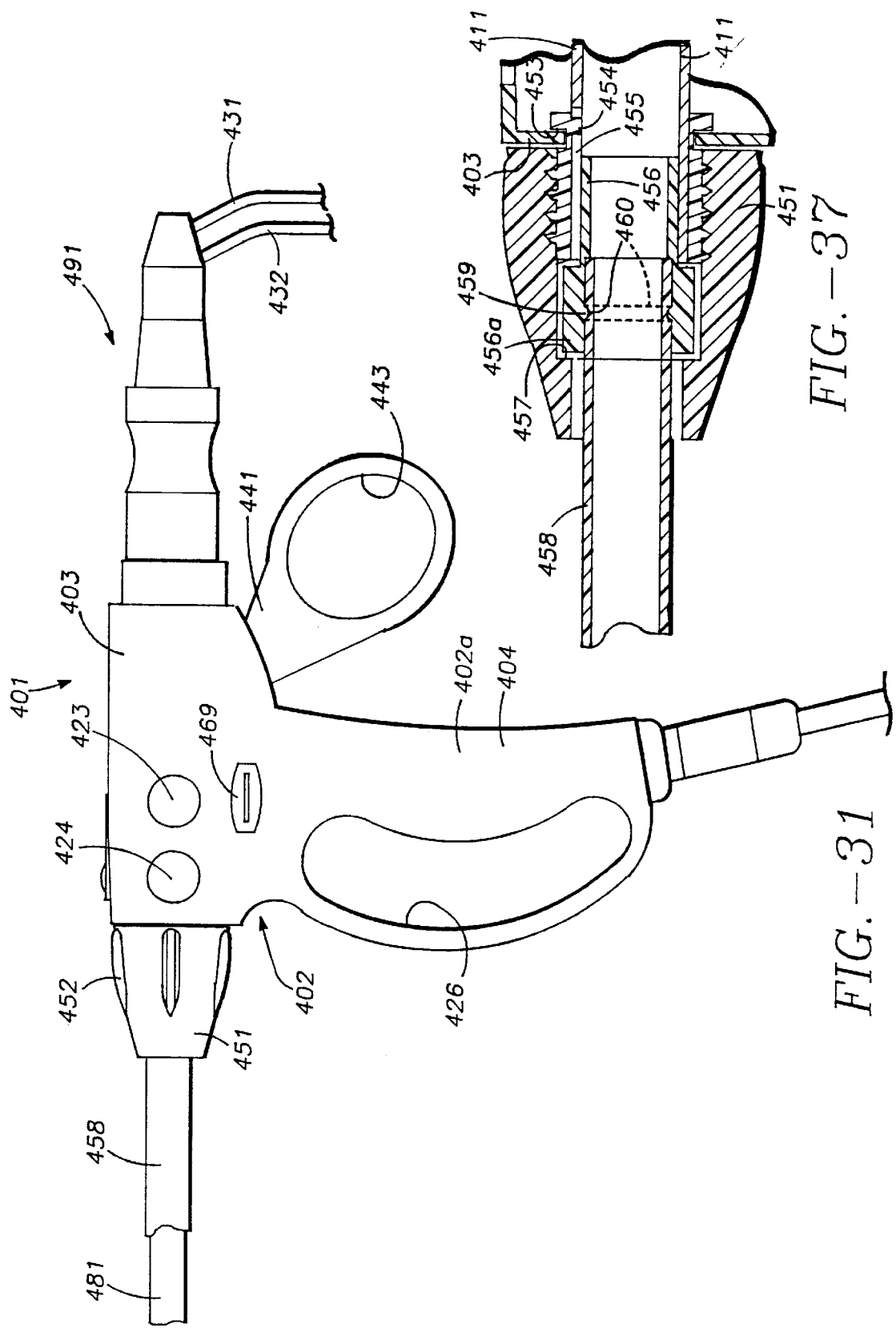

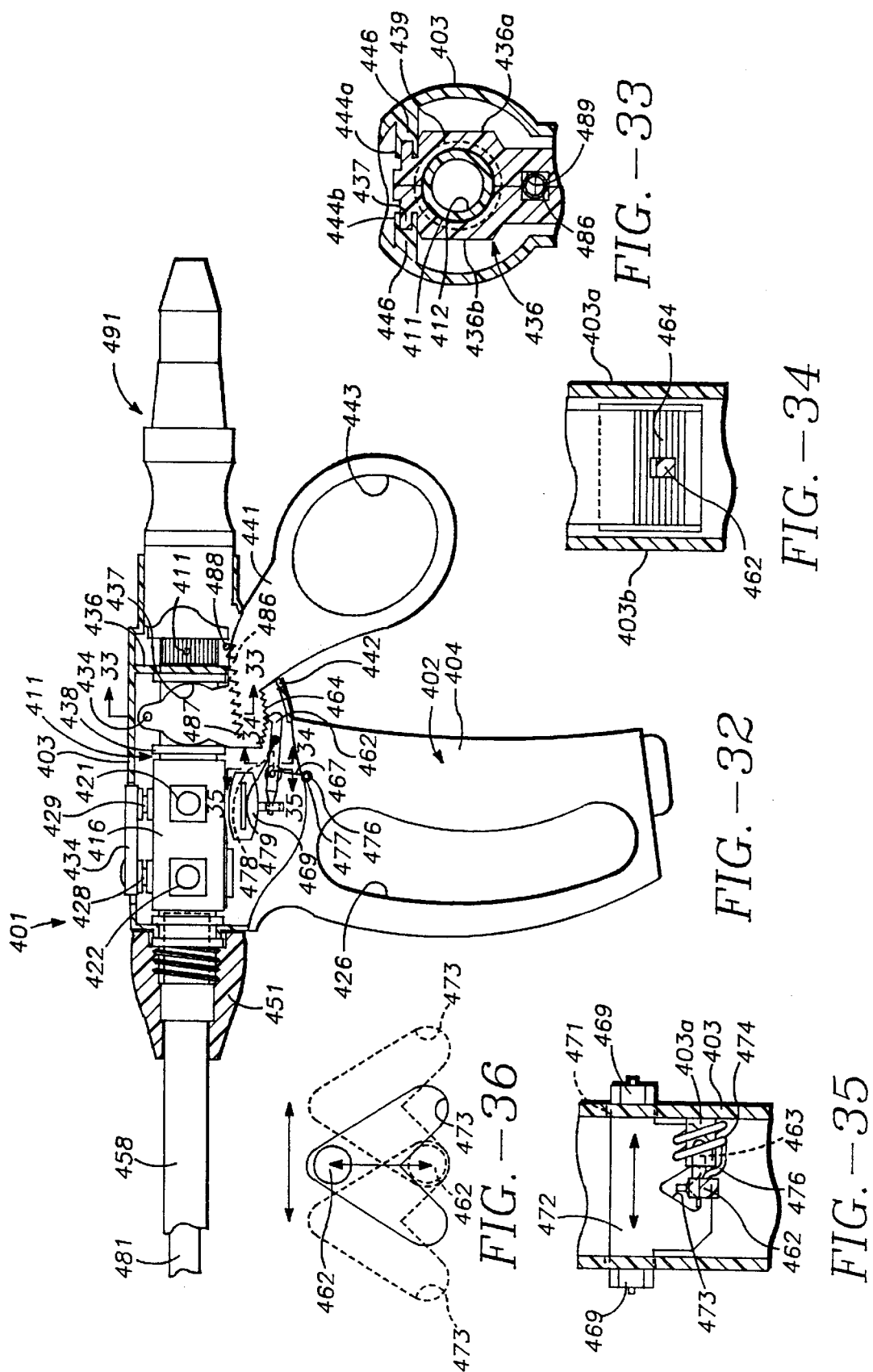

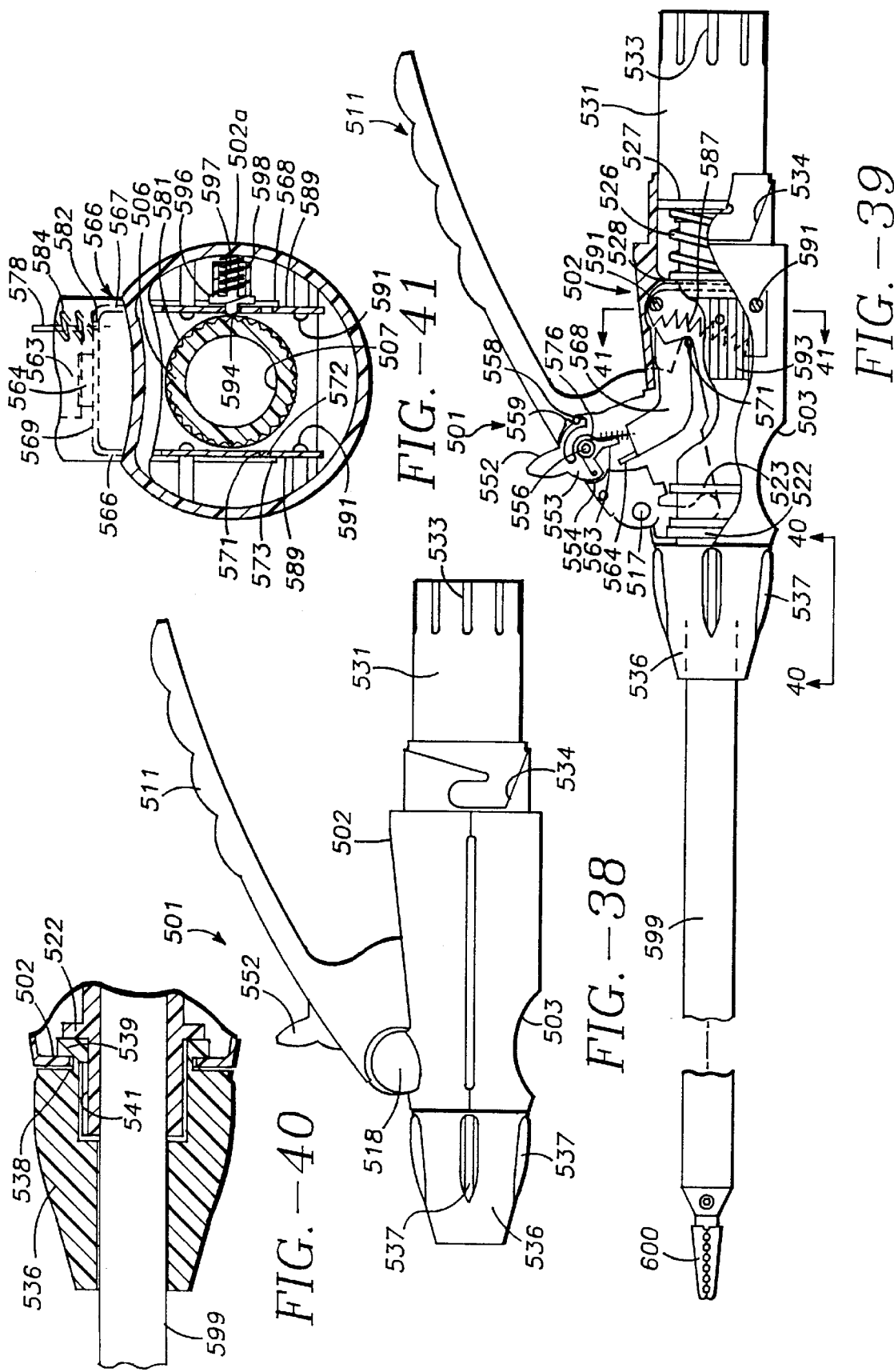

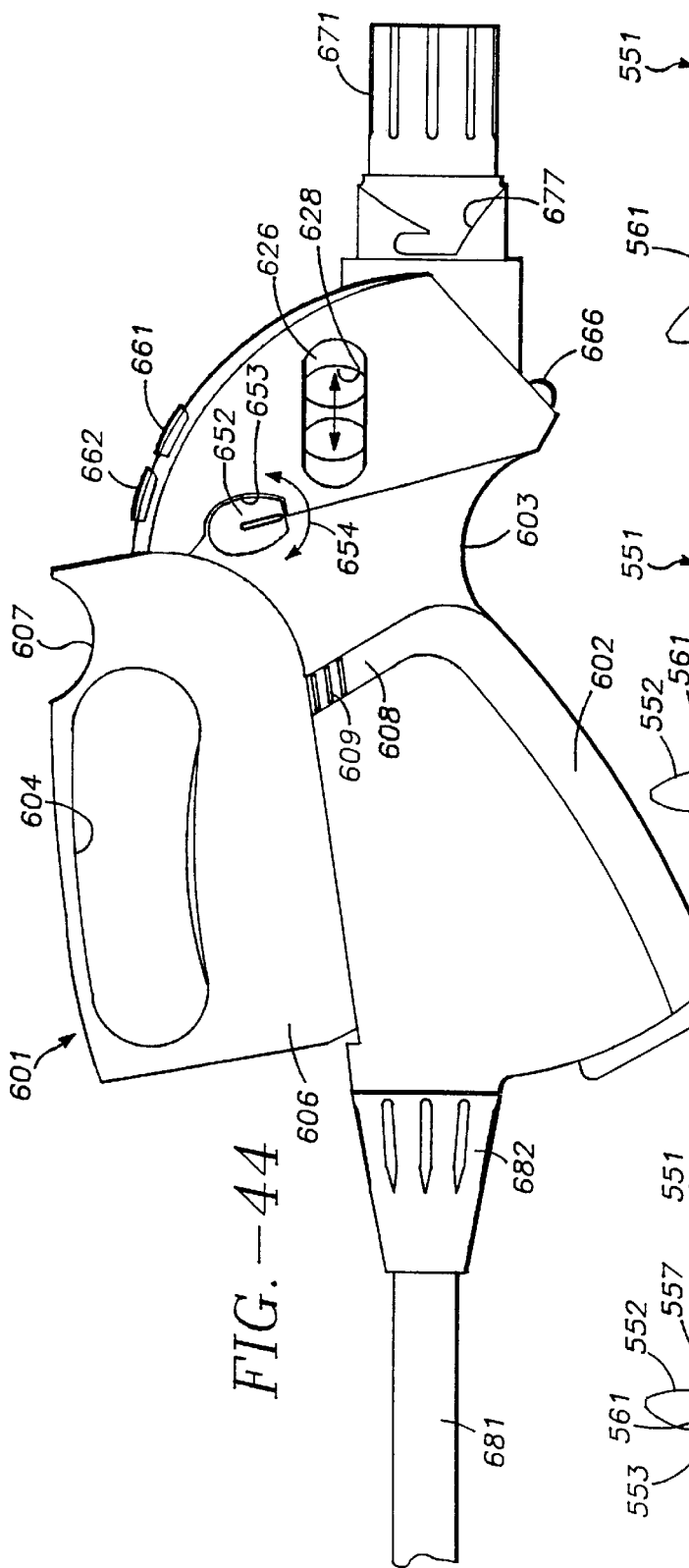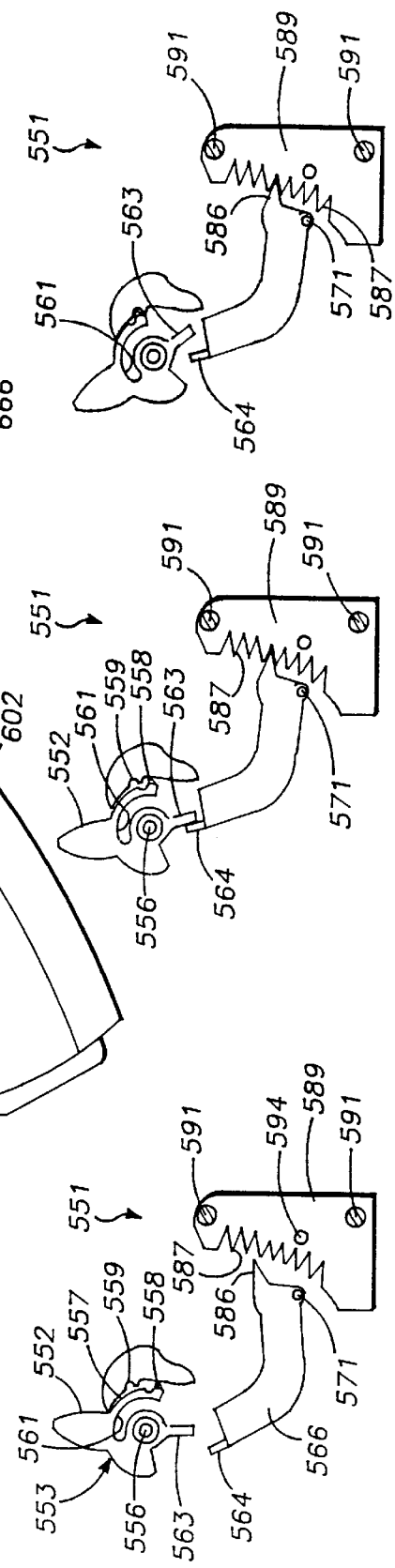

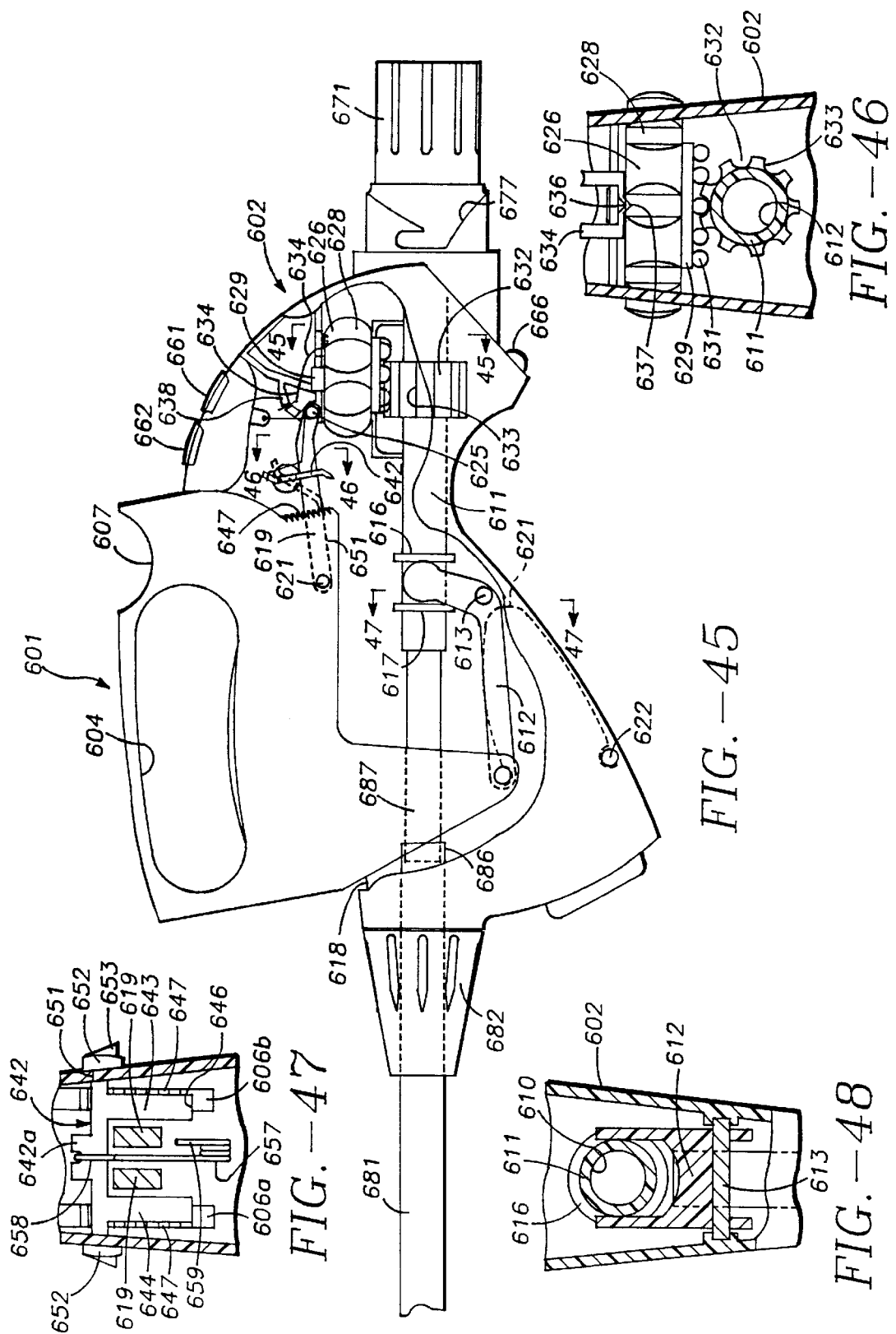

HAND-HELD SURGICAL DEVICE AND TOOLS FOR USE THEREWITH, ASSEMBLY AND METHOD

This is a division of application Ser. No. 08/282,892 filed Jul. 29, 1994 now U.S. Pat. No. 5,601,601, which is a continuation-in-part of application Ser. No. 07/806,666 filed on Dec. 13, 1991 now U.S. Pat. No. 5,433,725.

This invention relates to a hand-held surgical device and tools for use therewith, an assembly and method, and more particularly to such a device, tools, assembly and method for use in performing medical procedures.

Surgical devices for use in endoscopic procedures have heretofore been provided. These typically, however, have been separate individual devices or tools used independently. This is particularly true for tools for use in laparoscopy in which the tools usually have been expensive, fine precision metal tools. There is therefore a need for tools which are much less expensive which can be made disposable if so desired, and which can be utilized in conjunction with a hand-held surgical device.

In general, it is an object of the present invention to provide a hand-held surgical device and tools for use therewith, an assembly and a method for utilizing the same.

Another object of the invention is to provide a device of the above character which is provided with a hollow bore through which the tools can be inserted.

Another object of the invention is to provide a device of the above character in which the device includes a trigger mechanism for causing a linear thrusting motion which is utilized for actuating tools disposed in the bore of the device.

Another object of the invention is to provide a device of the above character in which the device includes a scissors-like mechanism for causing a linear thrusting motion which is utilized for actuating tools disposed in the bore of the device.

Another object of the invention is to provide a device of the above character in which the bore extends through a slidably mounted sleeve or barrel.

Another object of the invention is to provide a device of the above character in which the sleeve can be rotated.

Another object of the invention is to provide a device of the above character in which the tools can be locked onto the device for actuation of the tools and for rotation of the tool.

Another object of the invention is to provide a device of the above character in which tools can be readily inserted and removed.

Another object of the invention is to provide a device and tools for use therewith of the above character in which substantially fluid-tight seals are created between the tool and the device when a tool is inserted in the device.

Another object of the invention is to provide a device and tools for use therewith of the above character in which spring-loaded members are utilized.

Another object of the invention is to provide a device and tools for use therewith of the above character with which electrocautery operations can be performed.

Another object of-the invention is to provide a device and tools for use therewith in which the tools can be made disposable if desired.

Another object of the invention is to provide a device of the above character which can be sterilized.

Another object of the invention is to provide a device of the above character which is particularly suited for use in gynecological surgical procedures.

Another object of the invention is to provide a device of the above character which has been simplified and which has been provided with fewer functions to be used by a surgical assistant.

Another object of the invention is to provide a device of the above character which can be utilized by a surgical assistant which excludes electrical and fluid functions.

Another object of the invention is to provide a device of the above character which has a long lifetime and which has lower maintenance costs.

Additional objects and features of the invention will appear from the following description of the particular embodiment as set forth in detail in conjunction with the accompanying drawings:

FIG. 4 is a cross-sectional view taken along the line 4—4 of FIG. 2.

FIG. 5 is a cross-sectional view taken along the line 5—5 of FIG. 4.

FIG. 6 is a cross-sectional view taken along the line 6—6 of FIG. 4.

FIG. 7 is a cross-sectional view taken along the line 7—7 of FIG. 4.

FIG. 8 is a cross-sectional view taken along the line 8—8 of FIG. 1.

FIG. 9 is a cross-sectional view taken along the line 9—9 of FIG. 1.

FIG. 10 is a side elevational view of a tool incorporating the present invention.

FIG. 11 is a cross-sectional view of the tool shown in FIG. 10.

FIG. 12 is a cross-sectional view taken along the line 12—12 of FIG. 11.

FIG. 13 is a partial cross-sectional view of a device incorporating the present invention with a tool mounted therein.

FIG. 14 is a partial side elevational view partly in cross-section of the distal extremity of a tool incorporating the present invention.

FIG. 15 is a top plan view of the tool shown in FIG. 14 looking along the line 15—15 of FIG. 14.

FIG. 16 is a cross-sectional view taken along the line 16—16 of FIG. 14.

FIG. 17 is a cross-sectional view taken along the line 17—17 of FIG. 14.

FIG. 18 is a side elevational view of a distal extremity of another tool incorporating the present invention.

FIG. 19 is a view looking along the line 19—19 of FIG. 18.

FIG. 20 is a view of the distal extremity of another tool incorporating the present invention.

FIG. 21 is a top plan view looking along the line 21—21 of FIG. 20.

FIG. 22 is a partial side elevational view of another tool incorporating the present invention.

FIG. 23 is a plan view partially in cross-section looking along the line 23—23 of FIG. 22.

FIG. 24 is a partial side elevational view of the tool shown in FIG. 22 but of the side opposite that shown in FIG. 22.

FIG. 25 is a cross-sectional view taken along the line 25—25 of FIG. 23.

FIG. 26 is a cross-sectional view of the distal extremity of another tool incorporating the present invention.

FIG. 27 is a top partial plan view of another tool incorporating the present invention.

FIG. 28 is a cross-sectional view taken along the line 28—28 of FIG. 27.

FIG. 31 is a side elevational view of a hand-held surgical device incorporating another embodiment of the present invention utilizing a scissors-type actuation mechanism.

FIG. 32 is a side elevational view similar to FIG. 31 with certain portions broken away and shown in section.

FIG. 33 is an enlarged cross-sectional view taken along the line 33—33 of FIG. 32.

FIG. 34 is an enlarged cross-sectional view taken along the line 34—34 of FIG. 32.

FIG. 35 is an enlarged cross-sectional view taken along the line 35—35 of FIG. 32

FIG. 36 is an enlarged schematic view showing the manner in which the portion of ratchet mechanism shown in FIG. 35 operates.

FIG. 37 is an enlarged cross-sectional view of the nose cone portion of the device shown in FIG. 32.

FIG. 38 is a side elevational view incorporating another embodiment of a hand-held device particularly suitable for use by a surgeon's assistant.

FIG. 39 is a side elevational view of the device shown in FIG. 37 with a tool mounted therein and with certain parts broken away to shown certain parts in section.

FIG. 40 is a cross-sectional view taken along the line 40—40 of FIG. 39.

FIG. 41 is a cross-sectional view taken along the line 41—41 of FIG. 39.

FIGS. 43A, 43B and 43C are schematic representations showing the various modes of operation of the ratchet mechanism used in the device shown in FIG. 44.

FIG. 44 is a side elevational view of another embodiment of a hand-held surgical device incorporating the present invention particularly suitable for gynecological surgical procedures.

FIG. 45 is a side elevational view of the device shown in FIG. 43 with certain portions broken away.

FIG. 47 is a cross-sectional view taken along the line 45—45 of FIG. 44.

FIG. 47 is a cross-sectional view taken along the line 46—46 of FIG. 44.

FIG. 48 is a cross-sectional view taken along the line 47—47 of FIG. 44.

Figure 1:
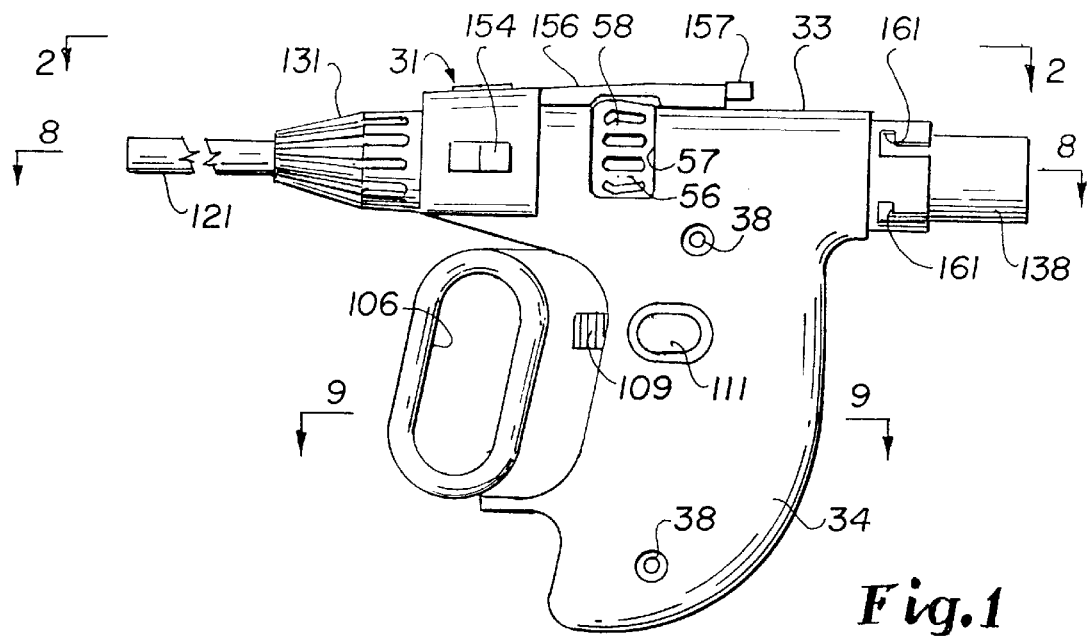
FIG. 1 is a side elevational view of hand-held surgical device incorporating the present invention.
Figure 2:
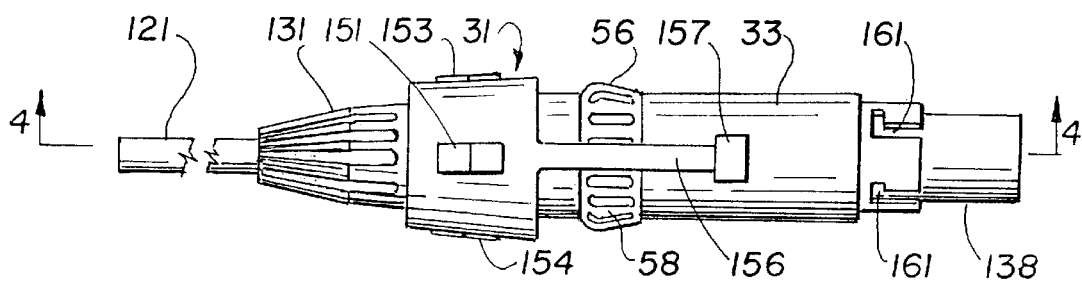
FIG. 2 is a top plan view looking along the line 2—2 of FIG. 1.
Figure 3:
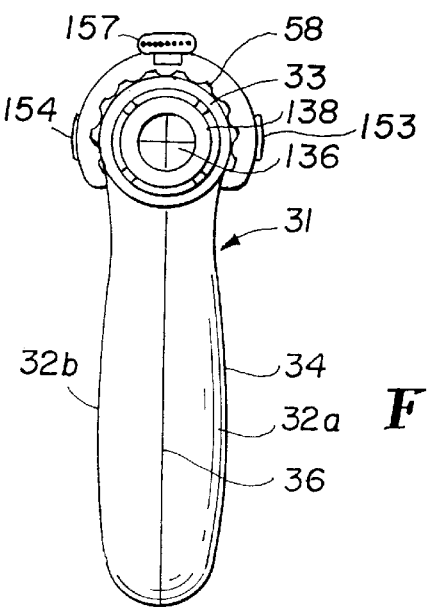
FIG. 3 is a rear elevational view looking along the line 3—3 of FIG. 1.

In general, the hand-held surgical assembly for use in performing a medical procedure is comprised of a hand-held endoscopy device having a bore extending therethrough. It also consists of a tool removably mounted in the bore. Cooperative means is provided for establishing a substantially fluid-tight seal between the bore and the tool. An adapter assembly is mounted on the tool.

More in particular, as shown in the drawings of FIGS. 1–9, the hand-held surgical device 31 consists of a housing 32 which is provided with an upper cylindrical portion 33 and a handle portion 34 in the form of a pistol grip adapted to be grasped and held by a single human hand. The housing 32 is preferably formed of a material which can repeatedly withstand autoclave sterilization, ethylene oxide sterilization or gamma radiation sterilization. One material found to be particularly suitable for this purpose is a plastic identified as Ultem, manufactured by the General Electric Company. Such a material is capable of withstanding high temperatures and is very durable. The housing 32, utilizing such a plastic, is formed in two parts 32a and 32b (see FIG. 3) which are joined together along a parting line 36. A pair of spaced apart bosses 37 (see FIG. 4) are provided on each of the parts 32a and 32b so that the two parts 32a and 32b can be fastened together by suitable means such as screws 38 extending into the bosses and forming the two parts 32a and 32b into a unitary housing 32.

An actuator tube assembly 41 is mounted in the upper cylindrical portion 33 for limited axial movement. The actuator tube assembly 41 is provided with a bore 42 which extends therethrough. The actuator tube assembly 41 consists of two tubes 43 and 44 in which tube 43 is formed of a suitable plastic such Ultem, hereinbefore identified, and the tube 44 is formed of a suitable metal such as stainless steel. The metal tube 44 has its proximal extremity fixed within the distal extremity of the plastic tube 43 so that the bore 42 is continuous and has the same diameter extending from the plastic tube 43 into the metal tube 44. The actuator tube assembly 41 is provided with proximal and distal extremities 46 and 47. These proximal and distal extremities 46 and 47 are axially guided within the housing by sidewise extending guide portions 48 and 49 (see FIG. 6) formed integral with the housing parts 32a and 32b having semicircular recesses 51 which are adapted to receive the proximal extremity 46 of the actuator tube assembly 41. Similarly, upper and lower guide portions 53 (see FIG. 4) formed integral with the parts 32a and 32b and having semicircular recesses 54 guide the distal extremity 47 of the actuator tube assembly 41.

Means is provided for rotating the actuator tube assembly 41 about its axis and consists of a thumb wheel or knob 56 (see FIGS. 1 and 4) which encircles the actuator tube assembly 41 and which extends through a slot 57 provided in the housing 32 so that the thumb wheel or knob 56 can be actuated by a finger of the hand while the hand is holding the pistol grip-shaped handle portion 34. The thumb wheel 56 is provided with spaced apart, axially extending raised portions 58 to facilitate frictional engagement by a finger of the wheel or knob 56. Cooperative mating means is provided between the thumb wheel 56 and the plastic tube 43 of the actuator tube assembly 41. The cooperative mating means consists of a pair of diametrically spaced apart axially extending keys 61 which are slidably mounted in the slots 62 extending diametrically outwardly from a bore 63 provided in the thumb wheel 56. The thumb wheel 56 is retained in a fixed longitudinal position with respect to the actuator tube assembly 41 by the guide portions 53 and wall portions 64 formed integral with the housing parts 32a and 32b, and having semicircular recesses 66 (see FIG. 4).

Means is provided for causing reciprocatory movement of the actuator tube assembly 41 for a suitable distance, as for example 0.125", and consists of yoke-like lever arm 71 formed of a suitable plastic such as Ultem. The yoke-like member 71 is provided with a pair of pins 72 extending from opposite sides thereof that are pivotally mounted in recesses (see FIG. 7). As can be seen, the pins 72 are provided at the upper extremity of the lever arm formed by the member 71 to provide a substantial mechanical advantage, as for example a 4-to-1 mechanical advantage. The upper extremity of the yoke-like lever arm 71 is provided with a U-shaped or forked portion 76 having generally circular upper extremities 77 (see FIG. 4), which are disposed on opposite sides of the plastic tube 43 between circumferentially extending spaced apart flanges 78 and 79 provided centrally of the plastic tube 43 of the actuator tube assembly 41. As can be seen from FIG. 4, the upper circular extremities 77 fit relatively closely within the flanges 78 and 79. The lower extremity of the yoke-like lever member 71 is pivotally connected to a trigger bar 81 by pin-and-slot connections in which elongate slots 82 are provided on opposite sides of the yoke-like member 71 that receive the opposite extremities of a pin 83 mounted in the trigger bar 81. The trigger bar 81 is mounted within the housing 32 for movement in a direction which is substantially parallel to the axis of the actuator tube assembly 41. The trigger bar 81 travels between upper and lower wall portions 86 and 87 which are formed integral with the housing parts 32a and 32b (see FIG. 5). In addition, the trigger bar 81 is guided by upper and lower guide portions 88 and 89 also formed integral with the housing parts 32a and 32b and which extend inwardly and slidably seat in grooves 91 and 92 provided on opposite sides of the trigger bar 81.

Spring means is provided for yieldably urging the trigger bar 81 to the left as viewed in FIG. 4 and consists of a leaf-spring 96 which has one leaf 97 engaging the interior of the housing 32 and the other end 98 engaging the lower extremity of the yoke-like member 71. The apex 99 of the spring can be secured if desired to the interior of the housing 32 by a screw 101. Means is provided for limiting the travel of the trigger bar 81 to the left in the housing 32 as viewed in FIG. 4, and consists of the yoke-like member 71 which restrains movement of the trigger bar 81 because of the limitations in axial movement of the actuator tube assembly 41 in the upper cylindrical portion 33.

The trigger bar 81 is provided with means whereby it is adapted to be grasped by fingers of the hand holding the handle portion 34. Such means consists of an elongate finger hole 106 which extends in a direction which is generally perpendicular to the axis of movement of the actuator tube assembly 41. It preferably is a size which is adapted to receive at least two fingers of the hand, as for example the two fingers between the index finger and the little finger or the index and middle fingers of the hand.

Means is provided for retaining the trigger bar 81 in a predetermined position against the force of the yieldable means provided by the leaf spring 96 and consists of elongate sawtooth portions 109 which are provided on opposite sides of the trigger bar 81. The portions 109 are adapted to be engaged by plungers 111 seated in a well 112 and extending through a hole 113 provided in the housing 32. Each of the plungers 111 is provided with two portions 111a and 111b with a space 114 therebetween and an annular recess 115 so that the portions 111a and 111b can be pressed together and snapped through the hole 113 and retained therein. The distal extremity of the plunger portion 111a is provided with sawteeth 116 which are adapted to engage the sawteeth of the sawtooth portions 109. A wave washer 117 is provided in each of the wells 112, and is utilized for yieldably returning the finger-operated plunger 111 into an out-of-engagement position. When the plunger 111 is engaged by a finger of the hand, as for example by the thumb on one side or the index finger on another side, the plunger 111 can be pushed inwardly against the force of the wave washers or springs 117 to cause the sawteeth 116 to engage the sawtooth portions 109 to retain the trigger bar 81 in a predetermined position. As soon as the sawteeth are engaged, the frictional engagement is sufficient to prevent the wave washers from returning a plunger ill to its home position. It is only when the trigger bar 81 is moved that the wave washers 117 will cause the sawteeth 116 to disengage and to permit a plunger 111 to return to its home position.

The surgical device 31 also includes a barrel 121 which is provided with a bore 122 extending axially thereof and through the barrel 121. The barrel 121 can be formed of a suitable material such as stainless steel. The bore 122 can be of a suitable size, as for example 8 mm. However, it should be appreciated that in connection with the present invention different barrels with different size bores can be provided, as for example ranging from 6 to 12 mm bores. The barrel can have a suitable length, as for example 8 to 14 inches. It is provided with a distal extremity 123 and a proximal extremity 124. The proximal extremity 124 is mounted within an adapter 126 of Ultem in the form of a reducer that is mounted in a metal tube 127 of a larger diameter. The diameter of the metal tube 127 is such so that the distal extremity of the metal tube 44 can slidably fit therein to provide a substantially fluid-tight seal between the same, to in effect form a trombone-type seal permitting the axial movement of the actuator tube assembly 41. The adapter 126 also forms a fluid-tight seal between the barrel 121 and the metal tube 127. The metal tube 127 is mounted in a fixed position with respect to the housing 32 and is frictionally retained therein as shown particularly in FIGS. 4 and 8.

A nose cone 131 formed of a suitable material such as Ultem is mounted over the barrel and serves to reinforce the connection between the barrel and the adapter 126 as well as the metal tube 127. The nose cone 131 is threadedly mounted as shown on the distal extremity of the housing 32.

The bore 42 is in axial alignment with the bore 122 provided in the barrel 121 and is adapted to receive tools of various types as hereinafter described. Cooperative means is provided for establishing a fluid-tight seal between the tool and the bore 32 and, as shown in FIGS. 4 and 8, consists of valve means in the form of a valve member of the type described in U.S. Pat. No. 5,141,498 dated Aug. 25, 1992. This valve member 136 is seated within a cylindrical enlargement 137 provided at the proximal extremity 46 of the plastic tube 43. A cylindrical cap 138 is threaded onto the cylindrical enlargement 137 (see Fig.8) to retain the valve member 136 in place. The cap 138 is provided with an annular shoulder 139 which engages the valve member 136 and holds it in place. The annular shoulder 139 is provided with serrations 140 on the proximal surface of the shoulder 139. The cap 138 is provided with a hole 141 which is in registration with the bore 42. The cap 138 is provided with a bore 142 in alignment with the hole 141. An annular recess 143 is provided within the bore 142.

The housing 32 is also provided with switching capabilities in the form of a switch 151 on the top of the housing 32 which serve electrocautery functions. Switch 151 has three positions, a "central or off" position, and two depressed or "on" positions on opposite sides of the central position. One side of switch 151 is for higher power for cutting and the other side of switch 151 is for lower power for coagulation. Control switches 153 and 154 are provided on opposite sides of the housing in general alignment with the switch 151 and also have three positions the same as switch 151. One side of control switch 153 can be utilized for controlling the introduction of fluids through the bore 42, as for example a saline or other irrigating solution which can be utilized for irrigating and cleansing the area of interest. The other side control switch 153 can be utilized to provide suction in the bore 42 to extract fluids, as for example saline solutions, which have been introduced for irrigation purposes as well as blood, bile, etc. The switch 154 can be utilized for controlling the same functions as switch 153. It can be seen that the switch 151 and the switch 153 have been positioned on the housing so that they can be readily depressed by the index finger on the right hand while the surgical device 31 is being held by the right hand. Similarly the switch 151 and switch 154 can be depressed by the index finger of the left hand when the surgical device 31 is being held by the left hand.

As hereinbefore pointed out the endoscopic device 31 is adapted to be used with tools of the type hereinafter described. In connection with such tools, cooperative mating means is provided whereby the tool is retained within the bore 42 and consists of L-shaped recesses 161 which are formed exteriorly on the cylindrical enlargement 137 of the tube 43. These recesses 161 are adapted to mate with cooperative mating means provided on the tool as hereinafter described. By utilizing cooperative mating means of this type in form of a bayonet-type connection, a tool can be inserted into the bore 42 and locked in place with a small rotational movement. It also can be readily removed by unlocking with a small rotational movement in an opposite direction and subsequent withdrawal.

As hereinafter described, a plurality of tools are adapted to be utilized with the endoscopic device 31. One of such tools is shown in FIGS. 10, 11 and 12. This tool 166 as shown therein consists of an elongate inner tubular member 167 which is provided with a bore 168 extending axially thereof and therethrough. The inner elongate tubular member can be formed of a suitable material such as stainless steel and can have a suitable exterior diameter such as 3 to 10 mm and by way of example 7 mm, and a suitable interior diameter of 2 to 9 mm and by way of example 6 mm. The tubular member 167 can have a suitable length, as for example ranging from 12 to 20 inches. It is provided with proximal and distal extremities 169 and 171.

A locking and actuation mechanism 172 is mounted on the proximal extremity 169. This mechanism 172 consists of an outer sleeve which is slidably mounted on the proximal extremity 169 of the inner tubular member 167. The proximal extremity of the sleeve 173 is fixed to a slider clip 174. The slider clip 174 is formed of a suitable material such as plastic and is provided with a serrated annulus 175 on its distal extremity adapted to engage the serrations 140 on the cap 138 of the hand held surgical device 31, the slider clip 174 is provided with a pair of arms 176 spaced 180° apart extending parallel to the axis of the sleeve 173. Additional arms 176 can be provided if a further distribution of linear forces is desirable. The arms 176 are substantially L-shaped and are provided with laterally extending legs 177 which extend into slots 178 provided in a cylindrical slider cap 179. The legs 177 are also provided with protrusions 180 which are rectangular in cross-section and extend outwardly so that they are adapted to seat in the annular recess 143 in the cap 138 as hereinafter described. The cylindrical slider cap 179 is provide with an inwardly and distally extending skirt 181 that is secured to the proximal extremity of the inner tubular member 167. Yieldable means in the form of a coil spring 182 is provided on the proximal extremity of the inner tubular member 167 and has one end engaging the skirt 181 and has the other end engaging the slider clip 174 (see FIG. 11).

An outer sleeve 183 formed of a suitable material such as Ultem is coaxially mounted on the slider cap 179 and engages a shoulder 184 provided on the slider cap 179, and is maintained in engagement therewith by a friction fit. The outer surface of the outer sleeve 183 is provided with an annular groove 186 which is arcuate in cross-section, as shown particularly in FIG. 10, that is disposed between the proximal and distal extremities of the outer sleeve 183. As shown in FIG. 11, the proximal extremity 187 is provided with an annular inclined surface 188 that overlies the outwardly extending legs 177 provided on the slider arms 176 to control their outward movement for purposes hereinafter described. The distal extremity 189 is provided with inwardly extending cylindrical protrusions 191 mounted thereon which are adapted to engage the L-shaped recesses 161 provided in the surgical device 31 for forming cooperative locking means between the same in the form of a bayonet-type lock.

A linkage 196 is provided in the tool 166 for actuating mechanisms of the type hereinafter described carried by the tool. This linkage 196 consists of a cylindrical pin 197 which extends diametrically through elongate slots 198 provided in the inner tubular member 167 and into holes 199 provided in the sleeve 173. The slots 198 have their elongations extending in the direction of the axis of the inner tubular member 167. A link rod 201 is mounted within the bore 168 of the inner tubular member 167 and is provided with a hole 202 through which the pin 197 extends. The link rod 201 extends distally from the pin 197 and is used for a purpose hereinafter described. The pin 197 is retained within the holes 199 by a plastic shrink tube 206 formed of a suitable heat-shrinkable plastic and extending over the sleeve 173. Another piece of shrink tube 207 is provided on the portion of the inner tube 167 which is exposed beyond the distal extremity of the sleeve 173 and covers all the distal extremity of the inner tubular member 167 except for a gap 208 which is provided to permit slidable axial movement of the sleeve 173 with respect to the tubular member 167. A mechanism 211 is mounted on the distal extremity of the inner tubular member 167 which is adapted to be operated by movement of the link rod 201 by sliding reciprocal movement of the outer sleeve 173 with respect to the inner tubular member 167.

Sealing means is provided in the proximal extremity of the slider cap 179 and consists of a valve member 216 of the type described in copending application Ser. No. 07/757,343, filed Sep. 10, 1991, which is clamped in place so that it is in generally axial alignment with the bore 168 of the inner tubular member 167. The valve member 216 is held in place by a cap 217 which threadedly engages a cylindrical extension 218 of the skirt 181 of the slider cap 179. A hole 219 is provided in the cap 217 which is in alignment with the valve member 216 and the bore 168. The valve member serves to form a substantially fluid-tight seal between the cap and the open end of the bore 168 provided in the inner tubular member 167.

The assembly 221 which is formed when a tool 166 is mated with an surgical device 31 is partially shown in FIG. 13. This view shows the manner in which the locking and actuator mechanism 172 of the tool 166 cooperates with the proximal extremity of the surgical device 31. The tool 166 is taken by one hand and the surgical device 31 is grasped by the other hand. The distal extremity of the tool is introduced through the bore 142 and through the valve member 136 and enters into the bore 42 and thence into the bore 122 of the barrel 121. As the locking and actuator mechanism 172 is advanced so that it comes into engagement with the proximal extremity of the housing 32, the tool 166 is rotated until the protrusions 191 come into engagement with the L-shaped recesses 161, then twisted slightly to lock the same into place by bayonet-type connection. At the same time, the proximal extremity of the cap 138 of the actuator tube assembly 41 is moved into the space between the outer sleeve 183 and the legs 177 until the protrusions 180 seat in the annular recess 143 of the cap 138 to lock the cap 138 to the slider clip 174. The serrated annulus 175 engages the serrations 140 on the shoulder 139 so that the tool 166 will be rotated when the actuator tube assembly 41 is rotated. As soon as this has been accomplished, the tool 166 has been locked onto the endoscopy device 31 so that the tool 166 is longitudinally fixed with respect to the endoscopy device 31. When the spool-shaped outer sleeve 183 is locked onto the proximal extremity of the housing 32 of the endoscopy device, the actuator tube assembly 41 can be moved axially with respect to the outer sleeve 183 and can be rotated with respect thereto.

The actuator tube assembly 41 is actuated by movement of the trigger bar 81 through the yoke-like member or lever arm 71 that has the circular extremities 77 disposed between the flanges 78 and 79. Movement of the actuator tube assembly 41, which in turn through its connection between the cap 138 and the protrusions 180 of the arms 176 seated in the annular recess 43 causes movement of the sleeve 173. Movement of the sleeve 173 causes movement of the pin 197 in the slots 198 in the inner tubular member 167 to cause movement of the actuator rod 201. As pointed out previously, only a relatively small amount of axial movement of the actuator tube assembly 41 is required and it is for this reason that the slots 178 and the slots 198 are of a relatively short length. As hereinafter explained, this movement is adequate to operate the mechanism 211 provided on the distal extremity of the tool 166. During the time that the movement of the sleeve 173 takes place, the inner tubular member is held stationary by its engagement with the skirt 181 which is connected by the bayonet-type connection hereinbefore described to the housing 32 of the endoscopy device.

Many of the tools 166 as hereinafter described utilize a common actuation mechanism 231 shown in FIGS. 14–17 that consists of first and second parallel links 232 and 233 which are pivotally connected by a large rivet to the distal extremity of the link rod 201. The other end of the link 233 is connected by a rivet 236 to the leg 237 of an L-shaped scissor blade 238. Similarly, the other end of the link 232 is connected by a rivet 239 to a leg 241 of an L-shaped scissor blade 242. The L-shaped scissor blades 238 and 242 are pivotally mounted on an Allen head screw 243 which is mounted in a tool tip 246 formed of a suitable material such as stainless steel.

The tool tip 246 is formed of parts 246a and 246b. Part 246a is semicircular in form as show in FIG. 16 and is provided with cylindrical recesses 247 to accommodate the rod 201 to permit reciprocatory movement of the rod 201 therein. The two parts 246a and 246b are mounted in the distal extremity of the tubular member 267 by suitable means such as a crimp fit in the form of annular grooves 248 in the distal extremity of the inner tubular member 167 as shown particularly in FIG. 14. The inner surfaces of the annular grooves 248 frictionally engage the tool tip 246 to retain it in place. The distal extremity of the tool tip 246 is provided with a slot 251 in which the blades 238 and 242 are disposed and which are connected to the links 232 and 233 in the manner hereinbefore described. The part 246b is provided with a well 252 which receives the Allen head screw 243 which is threaded into the part 246a a shown in FIG. 17 to thereby permit pivotal movement of the blades 238 and 242 with respect to the screw 243.

When a tool 166 is free and not disposed within an endoscopy device 31, the yieldable spring 182 will push the rod 201 in a direction towards the distal extremity to the solid-line position shown in FIG. 14 so that the blades 238 and 242 are in the closed position as shown in solid lines. When the tool is placed in the endoscopy device as hereinafter described, the sleeve 173 is moved proximal with respect to the tubular member 167 against the force of the yieldable spring 182 to move the rod 201 towards the proximal extremity to thereby move the rivets 234 to the right as viewed in FIG. 14 to cause the jaws 238 and 242 to be moved to the open dotted-line position shown in FIG. 14. Thereafter, the trigger bar 81 can be moved to actuate the rod 201 to move the scissor blades 238 and 242 to the closed position to perform cutting operations as hereinafter described.

Another tool 256 is shown in FIGS. 18 and 19 which has a proximal extremity which is substantially identical to the tool 166 hereinbefore described. The distal extremity is provided with an actuation mechanism 231 of the type utilized in the tool 166 in which L-shaped jaws 257 and 258 pivotally mounted on the screw 243 replace the L-shaped scissor blades 238 and 242. The jaws 257 and 258 are formed of a suitable material such as stainless steel and are provided with molded coverings 261 and 262 formed of a suitable material such as a hard durable polymeric material. These coverings 261 and 262 are provided with spaced apart serrations or teeth 263 extending transversely of the jaws 257 and 258. As shown in FIG. 19, the molded coverings 261 and 262 are formed to leave an elongate annular space 264 extending longitudinally of the jaw exposing the stainless steel jaws so that electrocautery functions can be performed as hereinafter explained. Similarly, a space 264 can be provided on the opposite side of the jaw also to serve electrocautery purposes.

Another tool 266 utilizing the actuation mechanism 231 hereinbefore described is shown in FIGS. 20 and 21 and is provided for obtaining biopsy samples. In this tool 266, oval-shaped clam shells 267 and 268 are provided which are pivotally mounted on the screw 243 and which are provided with lever arms 271 and 272 which are connected to the rivets 236 and 239. The clam shells 267 and 268 are formed of a suitable material such as stainless steel. The outer surfaces of the clam shells 267 and 268 can be covered by a layer 276 of an insulating material so that all that remains uncovered is a knife-edge like rim 277 on each of the clam shells to provide a space 278 therebetween through which electrical contact can be made to tissue to perform electrocautery operations as hereinafter described.

In FIGS. 22, 23 and 24 there is shown another tool 281. In this embodiment of the tool, the link member is in the form of a tubular sleeve 282 replacing the rod 201. The tubular sleeve 282 is slidably mounted within the inner tubular member 167 and has its proximal extremity secured to the pin 197 (see FIG. 23) so that as the pin 197 is moved longitudinally in the inner tubular member 167 the sleeve 282 will also be moved. A combination hook and scissor device 286 is mounted on the distal extremity of the inner tubular member 167. This hook and scissor device 286 consists of a fixed part 287 and a movable part 288. The fixed part 287 is provided with a knife edge 291 which is slightly offset upwardly as viewed in FIG. 24 from a line perpendicular to the axis of the inner tubular member 167. The knife edge 291 faces forwardly toward a notch 292 provided in the fixed part 287. The distal or forward extremity of the fixed part 287 is provided with a rounded distal extremity 293. The fixed part 287 is semi-circular in cross section as show in FIG. 25 and is fixed to the distal extremity of the inner tubular member 167 by suitable means such as solder (not shown). The movable part 288 is provided with a hook 296 on its distal extremity. The hook 296 is provided with a portion 296a which extends proximally into a cut out 297. The hook 296 is provided with a cutting edge 298 which extends perpendicular to the axis of the inner tubular member 167 which cooperates with the knife edge 291 provided on the fixed part 287. The movable part 288 is secured to the movable sleeve 282 and if desired can be formed integral herewith. A space 299 (see FIG. 23) is provided within the inner tubular member 167 to permit movement of the distal extremity of the sleeve 282 with respect to the proximal extremity of the fixed part 287. Placement of the tool 281 within the endoscopy device 31 causes the sleeve 282 to move to the left as viewed in FIG. 23 so as to move the cutting edge 298 across the knife edge 291 to the dotted-line position shown in FIGS. 22, 23 and 24.

A bore 301 is provided in the sleeve 282 and makes it possible to supply a liquid saline solution into the scissor device 286 in a manner hereinafter described.

Another tool 306 is shown in FIG. 26 in which the proximal extremity is similar to that hereinbefore described with respect to the tool 166 with the exception that the pin 197 has been eliminated. In this device, a right angle hook 307 formed of a suitable material such as stainless steel is provided. The hook 307 is mounted in the distal extremity of the inner tubular member 166 in a suitable manner such as by bonding the same into an insert 308 frictionally disposed within the distal extremity of the inner tubular member 167. The insert 308 is provided with a bore 309 that is in communication with the bore 168 in the inner tubular member 167 so that saline solutions can be introduced or suction can be applied to the bore 309 and the bore 168 during use of the tool 306.

Another tool 311 is shown in FIGS. 27 and 28 and serves as a spatula. It is provided with a spatula 312 in the form of a duckbill as shown in FIG. 27. The spatula 312 is formed of a suitable material such as stainless steel. It can be formed as a separate part or formed integral with a stainless steel cylindrical insert 313 which is frictionally retained within the distal extremity of the inner tubular member 167. The spatula 312 alternatively can be formed as a separate piece which can be welded to the cylindrical insert 313. It is inclined upwardly and toward the central axis of the tubular member 167 as shown in FIG. 28. Insert 313 is provided with a bore 314 which is in communication with the bore 168 in the inner tubular member 167 so that the saline solution can be introduced through the bore 314 or alternatively suction can be applied through the bore 314.

Figures 29, 30:
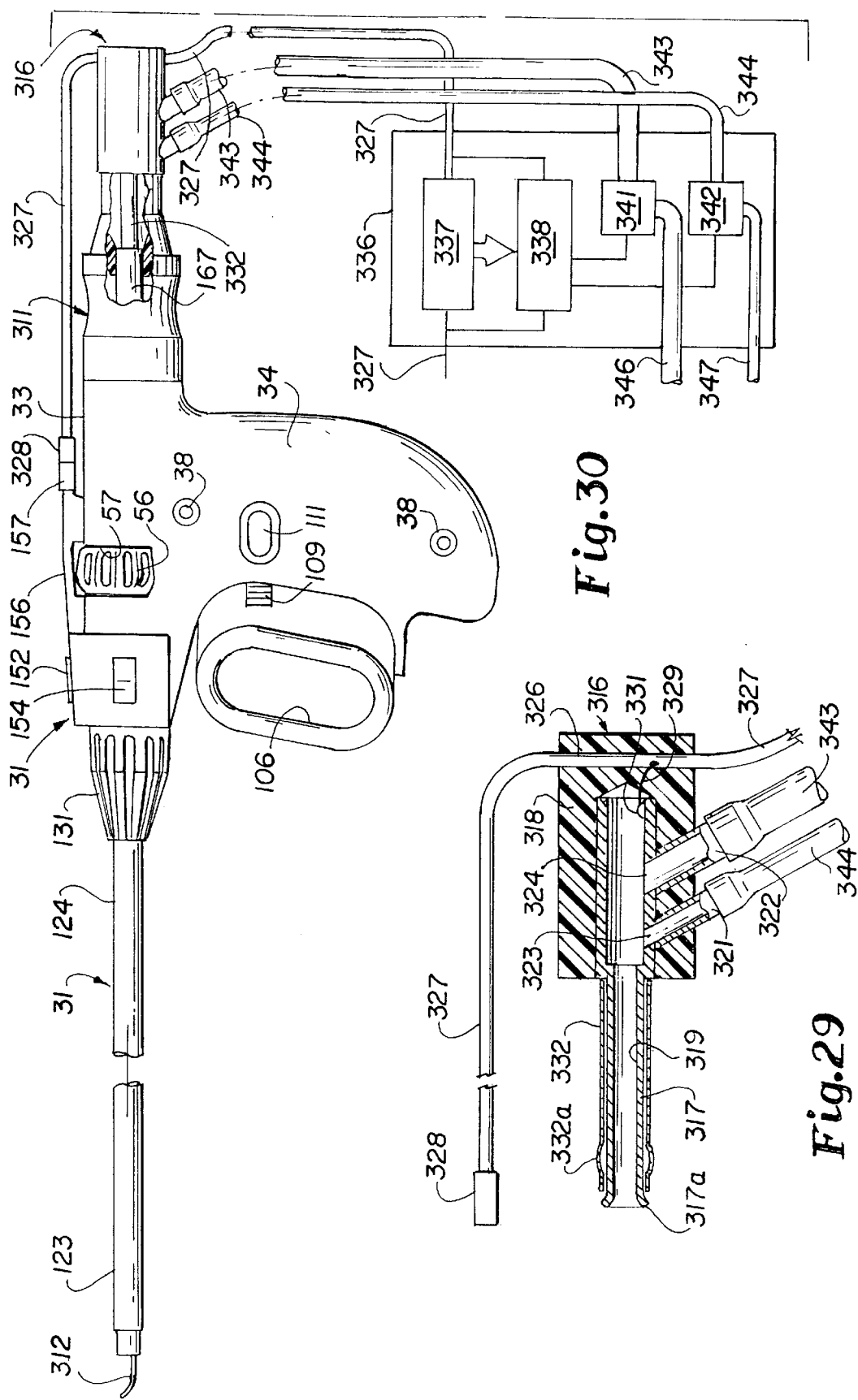
FIG. 29 is a cross-sectional view of an adapter assembly for use with a tool when it is inserted into an endoscopy device of the present invention.
FIG. 30 is a side elevational view of an assembly incorporating the present invention in which a tool is inserted into an endoscopy device and in which an adapter assembly is mounted in the tool.
Figure 42:
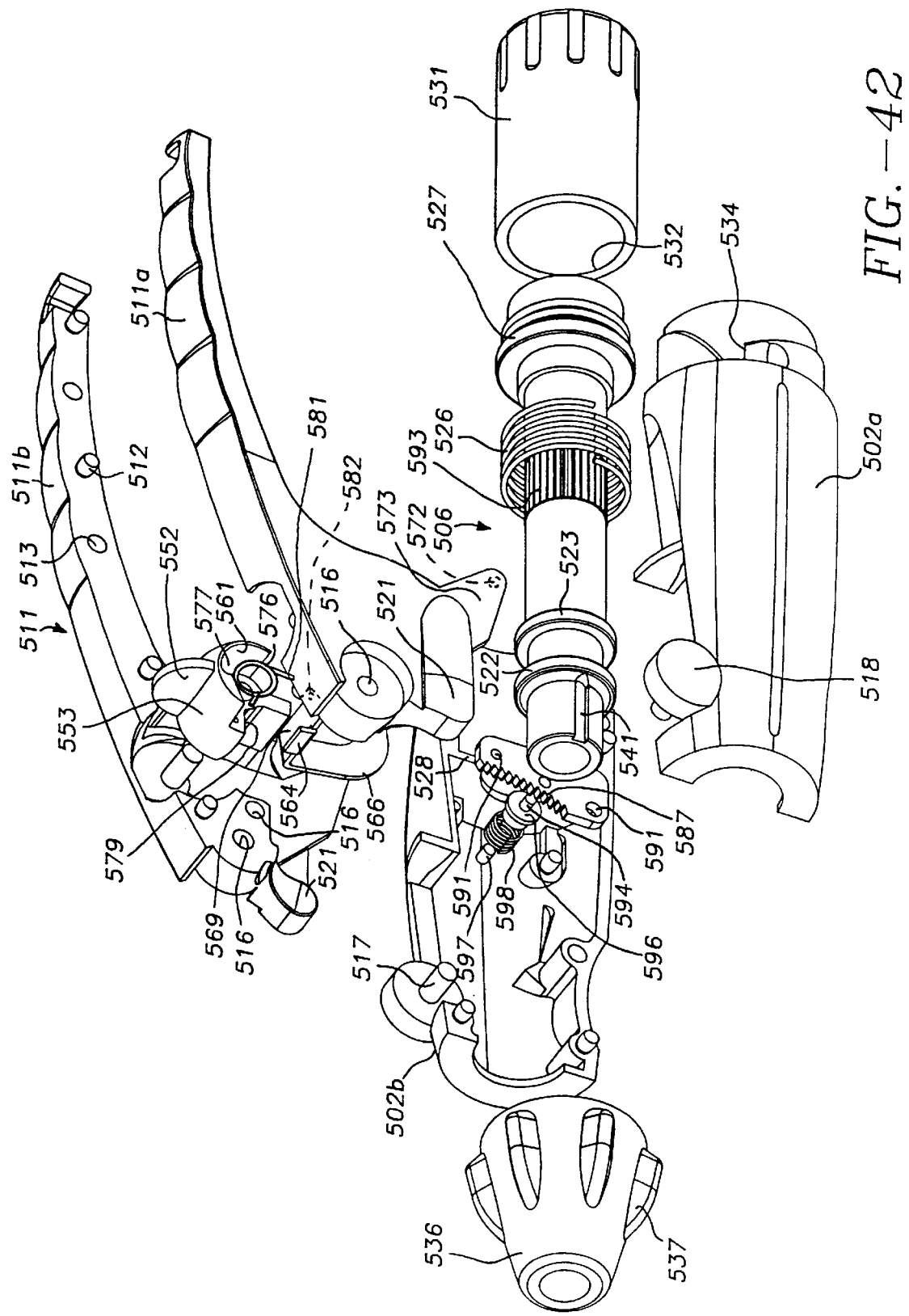
FIG. 42 is an exploded isometric view of the device shown in FIG. 37.

An adapter assembly 316 which is a type which can be utilized with the tools hereinbefore described and particularly with respect to tool 311 shown in FIGS. 27 and 28 is shown in FIG. 29. This adapter assembly 316 consists of a cylindrical sleeve 317 formed of a suitable material such as stainless steel which is provided with a hub 318. A cylindrical bore extends through the cylindrical sleeves 317 and into the hub 318. Fittings 321 and 322 are mounted on the hub 318 and are provided with flow passages 322, 323 and 324 that are in communication with the bore 319. A covering 226 formed of a suitable insulating material such as plastic is provided over the hub 318 and has molded therein an electrical cable 327 that is provided with multiple conductors as for example seven which extend to a multiple-pin connector 328. The electrical cable 327 also carries another high voltage conductor wire 329 which is utilized in electrocautery procedures as hereinafter described and is electrically connected to the hub 318 by suitable means such as by a solder joint 331. The distal extremity of the cylindrical sleeves 317 is swaged outwardly as shown in FIG. 29 to hold the adapter assembly 36 in place in a tool as hereinafter described. Means is provided for making electrical contact between the inner tubular member 167 and the sleeve 317 and consists of another sleeve 332 formed of a suitable material such as brass which is disposed on the exterior surface of the cylindrical sleeve 317 and extends from the hub 318 to the swaged portion 317*a*. The sleeve 332 is provided with an annular bulge-like portion 332*a* to facilitate making electrical contact with the inner tubular member 167 while permitting rotation of the inner tubular member 167 with respect to the sleeve 332.

As shown in FIG. 30, the adapter assembly 16 is adapted to be mounted in the tool 311 and can be advanced through the hole 219 in the cap 17 through the valve member 216 and into the inner tubular member 267 so that the swaged portion 317 makes good electrical contact with the interior of the inner tubular member 167. At the same time, communication is established between the bore 319 and the bore 168 of the tubular member 167. The connector 328 is connected to the connector 157 provided on the endoscopic device 37.

As shown in FIG. 30, a control console 336 is provided for use with the adapter assembly 316. The control console 336 is provided with a microprocessor 337 and relay control assembly 338. The microprocessor 337 and the relay control assembly 338 are connected to a suitable source of power by a cable 339. The microprocessor 327 and the relay panel 338 are connected to the cable 327. The relay panel 338 is also connected to electrical solenoids 341 and 342. The solenoids 341 and 342 are utilized for controlling the flow of fluids to and from the adapter assembly 316. Thus solenoid 341 is provided with a tube 343 which is connected to the fitting 322 provided on the adapter assembly 316 and solenoid 342 is provided with a tube 344 which is connected to the fitting 321 of the adaptor assembly 316. The solenoid 341 is connected to a suitable source of saline solution by a tube 346 and similarly the solenoid 342 is connected to a source of vacuum by tube 347.

Operation and use of the hand held surgical device and tools for use therewith, the assembly thereof and the method may now briefly be described as follows. Let it be assumed that the patient has been prepared and draped for performing a medical procedure, as for example a laparoscopy for removing a diseased gallbladder. The surgeon places a puncture in the abdomen with a small tool such as a veres needle. Carbon dioxide is introduced into this puncture to cause a partial inflation of the abdomen to thereby create a cavity in the abdominal area. The Veres needle can then be removed, and a trocar can be introduced into the abdomen through the same puncture or in a position adjacent to the needle. The trocar can be of a conventional type or can be of the type described in U.S. Pat. No. 5,176,648 dated Jan. 5, 1993. With the trocar in place, additional carbon dioxide is introduced into the abdomen to further inflate the abdomen to a pressure corresponding to approximately 15 mm of mercury. With the abdomen so inflated, an endoscope is inserted into the abdominal cavity so that the interior of the abdominal cavity can be visualized on a video monitor. Thereafter, three additional trocars are positioned in the abdomen, one adjacent the patient's upper left-hand portion of the abdomen, another at the upper right-hand portion of the abdomen, and the third at the lower right-hand portion of the abdomen. These additional sites are used for introduction of various tools typically utilized during endoscopic surgery. For example, the four trocars thus far described would be utilized to remove a gallbladder. The surgeon, after the trocar is in place, takes the endoscopy device 31 of the present invention and grasps it by either his right hand or left hand by grasping the pistol grip-handle portion 34. The surgeon then positions the barrel 121 so that it can enter the trocar and be advanced into the abdomen while the interior of the abdomen is being visualized on the video monitor. The surgeon then selects the desired tool to be utilized with the endoscopy device 31. For example, the first tool the surgeon may select may be a grasper of the type shown in FIGS. 18 and 19. With the grasper 256 locked in place in the endoscopy device 31, the surgeon can manipulate the grasper 256 to manipulate the liver and/or the gallbladder by grabbing onto one of the organs and pulling on it or pushing on it so that the desired positions of the organs are achieved to permit the surgeon to perform the gallbladder removal procedure.

The grasper 256 in its normal position has its jaws 257 and 258 in a closed position. With the jaws in the closed position, the grasper can be inserted through the barrel 121 and the tool locked in place by the cap 138 being advanced between the interior of the slider cap 179 and the legs 76 until the protrusions 180 snap into the annular recess 143 to lock the tool in place. This serves to connect the tool mechanism to the trigger mechanism. Thereafter, upon slight additional inward movement of the grasper 256 the bayonet-type lock connection is made by the protrusions 202 entering into the L-shaped recesses 161 and then with a slight grasper 256 it is locked into place. After this has been accomplished, the trigger bar 81 can be operated by having the fingers of the hand extend through the hole 106 to cause opening and closing of the jaws 257 and 258. When the tool 256 is locked into position as hereinafter described, the jaws 257 and 258 are moved to an open position and thereafter can be opened and closed by the surgeon operating the trigger bar 81.

Movement of the trigger bar from ½ to ⅝" causes approximately ⅛" of travel of the actuator tube assembly 41, which movement is utilized to cause opening and closing of the jaws 257 and 258. Because of the approximately 4-to-1 mechanical advantage which is achieved, the application of one pound of force by the surgeon to the trigger bar 81 will cause the application of approximately 4 pounds of force by the inside surfaces of the grasper jaws 257 and 258. The mechanism for operating the jaws 257 and 258 is one in which pushing of the rod 201 serves to cause closing of the jaws and pulling of the rod 201 causes opening of the jaws 257 and 258. The mechanical advantage is maximized at the point of closure, which is achieved by the pushing toggle action.

After the physician has positioned the liver and gallbladder in the desired positions to achieve access to the desired anatomy, the surgeon can then utilize another tool, as for example another grasper 256, and insert it through one or the other ports to dissect the fatty tissue which is connected to the gallbladder and which is also connected to the cystic duct and to the cystic artery. After the fatty tissue has been pulled away from the desired ducts and arteries, the grasper 256 can be removed from the endoscopy 31 device by giving a slight twist to the tool or grasper 256 to cause the protrusions 191 to move out of engagement with the L-shaped slots 161 and then pulling the tool rearwardly. As the tool is pulled rearwardly, the outer sleeve 183 with its inclined surface 188 urges the arms 176 inwardly so that the protrusions 180 clear the annular recess 143 in the cap 138 to permit separation of the tool from the endoscopy device 31. The tool can be readily removed through the valve member 136 with the valve member 136 retaining a fluid-tight engagement with the tool and, after the tool has been removed, to continue to form a fluid-tight seal with respect to the bore 42 to prevent the escape of carbon dioxide.

Thereafter, the surgeon can take another tool such as a scissors 166 and insert it into the endoscopy device 31 in the same manner in which the grasper tool 256 has been inserted and locked into place. After this has been accomplished, the surgeon can operate the trigger bar 81 of the scissors 166 to cause opening and closing of the scissors to cut a pathway through the cystic duct.

A catheter (not shown) can then be introduced by the surgeon through another trocar and advanced into the ductwork. A radiopaque dye can then be introduced through the catheter into the ductwork, and by viewing the same under x-ray the surgeon can ascertain whether or not in fact he has cut the cystic duct. Assuming that the cystic duct has been severed as desired, another tool can be introduced through a trocar such as a clip applier to apply clips to close the cystic duct. A similar procedure can be utilized for cutting the artery and clipping the same. Once the cystic duct and the artery have been legated, the doctor can cut through the cystic duct and the artery without fear of causing internal bleeding. The gallbladder can then be dissected from the liver by use of the scissor tool 166, the hook 306 or the spatula 12.

In the removal of the gallbladder it may be desirable to use an additional tool or another tool such as the spatula tool 311 shown in FIGS. 27 and 28 with an adapter assembly 316 mounted thereon. After the spatula tool 311 has been introduced into the endoscopy device 31 and locked in place, the spatula 12 can be manipulated to separate the gallbladder from the liver by physical separation utilizing the spatula. Alternatively, electrocautery techniques can be utilized in conjunction with the spatula 312 which by operation of the switches 151 and 152 can be used to burn away the undesired tissue and to perform electrocautery where necessary. The electrical arcing created between the spatula and the tissue will cut through and coagulate away the connective tissue between the gallbladder and the liver. In this way, the gallbladder can be systematically dissected free from the liver.

In the event that there is excessive bleeding or holes are cut into either the gallbladder or the liver, it may be necessary to cauterize and cleanse the area in order to permit the surgeon to continue to visualize the operations being performed. This can be readily accomplished by introducing a saline solution by operating one of the switches 153 or 154 provided on the sides of the housing 32 of the endoscopy device. These switches can be operated by the fingers of the hand holding the tool. Thus, first, a saline solution can be introduced into the adapter assembly 316 through the energization of the solenoid 341 to cause fluid to pass into the bore 168 of inner tubular member 167 and through the bore 314. Similarly, suction can be applied to these same passages by energization of the solenoid 342 to cause the saline solution and other liquids in the cavity to be withdrawn from the patient. This can be readily accomplished because of the relatively large-diameter flow passages provided for introducing liquids such as saline solutions and removing liquids from the abdominal cavity.

After the liquids have been removed from the cavity, the surgeon is free to continue the procedure, as for example continuing dissection or removal of the gallbladder from the liver.

After the gallbladder has been separated from the liver, it can be removed from the abdominal cavity through one of the puncture wounds which has been formed in the abdominal wall. Alternatively, the surgeon can utilize a retrieval device such as that disclosed in U.S. Pat. No. 5,190,555 dated Mar. 2, 1993, which can be introduced through one of the punctures and the gallbladder and its contents placed into the sack. The sack can then be closed and the sack with its contents, namely the gallbladder, bile and stones, can then be pulled through the abdominal puncture or wound. After the gallbladder has been removed, the other trocars can be removed, as well as the endoscope. The abdomen is then deflated or desufflated. The puncture wounds in the abdomen are then closed with one or more sutures.

In the procedure hereinbefore described, any of the tools hereinbefore described can be utilized in the procedure, as for example the hook scissors tool 286 shown in FIGS. 22–25. Many of the tools can be utilized as electrocautery devices because of the metal distal extremities can form electrical contact with the tissue on which electrocautery operations are to be performed. As explained previously, the adapter assembly 316 can be readily secured to the tool while maintaining a fluid-tight connection with the same through the valve member provided in the tool. Saline introduction and suction operations also can be readily performed. It should be appreciated that surgical device 31 and the tools hereinbefore described can be constructed of non-ferrous materials such as plastic, aluminum, brass, etc., thereby permitting them to be used in conjunction with magnetic resonance imaging, x-rays, CT scanning, ultrasound and other imaging techniques.

Another embodiment of a hand-hand surgical device 401 incorporating the present invention is shown in FIGS. 31–36 which is provided with a scissors-type hand actuation mechanism rather than a trigger-type hand-actuator mechanism disclosed in the previous embodiments of the handheld surgical device. The surgical device 401 consists of a housing 402 formed in two parts 402a and 402b, each of which has a cylindrical portion 403 and a descending handle portion 404. The two parts 402a and 402b are adapted to be fitted together in a suitable manner such as by push ins (not shown) extending into holes (not shown) provided in the parts 402a and 402b. An actuator tube assembly 411 of the type hereinbefore described is mounted in the upper cylindrical portion 403 for limited axial reciprocatory movement. The actuator tube assembly 411 is provided with a bore 412 which extends therethrough. The actuator tube assembly 411 is constructed with a trombone-like seal in a manner substantially similar to that hereinbefore described with the previous embodiments and thus will not be described in detail.

The actuator tube assembly 411 extends through a rectangular box-like electrical housing 416 mounted in the upper cylindrical portion 403 of the housing 402 (see FIG. 32). The electrical housing 416 is adapted to interact with a flex circuit (not shown) of the type described in co-pending application Ser. No. 08/128,309 filed on Sep. 28, 1993 now U.S. Pat. No. 5,512,721. The flex circuit is connected to two electrical switches 421 and 422 mounted on each of the opposite sides of the housing 416 for "cut" and "coag" functions which are adapted to be operated by push buttons 423 and 424 provided on opposite sides of the cylindrical housing 403. The push buttons 423 and 424 are adapted to be operated by a finger of the human hand holding the hand-held surgical device and having the other three fingers extend through the arcuate slot 426 provided in the handle portion 404. This arrangement makes the hand-held surgical device 401 ambidextrous so it can be operated equally well by left-handed or right-handed persons. Two other electrical switches 428 for irrigation and 429 for suction are carried by the electrical housing 416 and extend upwardly through the cylindrical portion 403 and are used for controlling the introduction of saline solution through a tube 431 connected to the device 401 and a tube 432 for supplying suction to the device. These two switches are controlled by a rocker switch arm 434 accessible from the top of the cylindrical portion 403 of the housing 402 and also being adapted to be engaged by the index finger of the hand holding the surgical device 401.

Means is carried by the housing 402 for causing reciprocatory movement of the actuator tube assembly 411 consists of a yoke-like member 436 which is provided with rounded extremities 437 that engage spaced-apart parallel annular flanges 438 and 439 carried by the actuator tube assembly 411. The yoke-like member is provided with handle portions 441 which extend through a slot 442 provided in the cylindrical portion 403 of the housing 402 proximal of the handle portion 404. The handle portions 441 are provided with holes 443 adapted to receive the thumb of the hand engaging the handle portion 404.

The yoke-like member 436 is pivotally mounted in the cylindrical portion 403 of the housing 402 by pin 444 formed of boss portions 444a and 444b which are seated in inwardly extending protrusions 446 provided as a part of the cylindrical portions 403a and 403b.

A nose cone 451 is disposed in the forward extremity of the housing 402. It is threaded onto a cylindrical nose bearing 452 (see FIG. 37). The nose bearing 452 is provided with an annular recess 453 into which the cylindrical portion 403 extends to permit longitudinal movement of the actuator tube assembly 411. The nose bearing 452 is mounted on the distal extremity of the actuator tube assembly 411. Cooperative mating means is provided for causing rotation of the actuator tube assembly 411 as the nose cone 451 is rotated by a finger of the hand as for example by the index finger as the hand-held surgical device 401 is held by a human hand. Such cooperative mating means takes the form of a key and slot connection in which a key 454 is carried by the nose bearing 453 and extends into an elongate slot 455 carried by the actuator tube assembly 411 (see FIG. 37). This key and slot connection, in addition to 10 causing rotation of the actuator tube assembly 411 permits longitudinal or axial movement of the actuator tube assembly relative to the nose cone 451. A nose bushing 456 is slidably mounted on the distal extremity of the actuator tube assembly 411 and is provided with a flanged portion 456a extending beyond the distal extremity of the actuator tube assembly 411. This flange portion is rotatably mounted in an annular recess 457 provided on the distal extremity nose cone 451. A cylindrical barrel 458 is releasably retained within the nose bushing 456 by a snap-in type of connection comprising an annular bead 459 which is adapted to seat in an annular recess provided on the proximal extremity of the barrel 458 (see FIG. 37). With the construction hereinbefore described, it can be seen that the barrel 458 can remain stationary when the nose cone 451 is being rotated for causing rotation of a tool carried within the barrel 458 as hereinafter described.

A passive ratchet mechanism 461 is provided for retaining the actuator tube assembly 411 in a desired axial position as it is advanced by operation of the thumb handle 441. This ratchet mechanism 461 takes the form of a ratchet pawl 462 pivotally mounted in a boss 403a (see FIG. 35) in the housing 402 by a pin 463 extending transversely thereof. Ratchet pawl 462 is adapted to engage ratchet teeth 464 carried by an arcuate surface 466 provided on the thumb handle 441.

A cam mechanism 468 is provided for causing the ratchet pawl 462 to engage the ratchet teeth 464 and consists of push buttons 469 accessible from opposite sides of housing 402. The buttons 469 have portions thereof extending through slots 471 connected to a cam member 472 (see FIG. 36) which is movable sidewise in opposite directions within the housing 402. The cam member 472 is provided with a vee-shaped slot 473 with the legs thereof extending downwardly formed therein. One end of the ratchet pawl 462 opposite the pivot pin 463 extends into the vee-shaped slot (see FIGS. 35 and 38) and is centered at the apex of the vee-shaped slot. In this position of the cam member 472, the pawl 462 is maintained out of engagement with the ratchet teeth 464. A coil spring 474 is mounted on the boss 403a and has an end 476 engaging another boss 477 on the handle portion 404 and the other end 478 engaging a boss 479 on the ratchet pawl 462. The coil spring 474 yieldably urges the cam member 472 so that the apex of the vee-shaped slots brings the ratchet pawl 462 to the central dotted-line portion shown in FIG. 36.

If it is desired to passively engage the ratchet teeth, either of the buttons 469 can be engaged by a finger of the hand and the cam member 472 is pushed sidewise. As this occurs, the end of the pawl 462 remote from the ratchet teeth is cammed downwardly with respect to the pivot point 463 with the other end being cammed upwardly to engage the ratchet teeth 464. Thus it can be seen that any time that the device 401 is being utilized and the thumb is being utilized for operating the thumb handle 441 to bring it in closer proximity to the handle portion 404, the ratchet teeth are advanced forwardly and the ratchet mechanism 461 can be utilized to retain the thumb handle 441 in a desired position by merely engaging one of the push buttons 469 to cause the end of the pawl 462 opposite the portion of the pawl 462 engaging the teeth to be cammed downwardly to move the pawl into engagement with the teeth to latch the thumb handle 441 in a desired position. It can be seen that this procedure can be accomplished either with a button on each side depending on whether the person is right-handed or left-handed. In both cases movement, because of the vee-shaped slot 472, the extremity of the ratchet pawl 462 therein will be cammed downwardly against the force of spring 474 to urge the ratchet pawl 462 into engagement with the ratchet teeth 464. When it is desired to release the pawl 462 from the ratchet teeth 464, it is merely necessary to engage the thumb handle 441 and push on it slightly to release the ratchet pawl 462 permitting the spring 474 to return the cam member 472 to a central position and permitting the ratchet pawl to remain disengaged. The thumb handle 441 can be released to be yieldably returned to its home position in which the actuator tube assembly 411 is located in a proximal position by a return spring 486 which has one end secured within the thumb handle 441 in a suitable manner such as by a pin 487 and which has the other end secured to the housing 402 by a pin 488. As can be seen from FIG. 33, the return spring 476 extends through a hole 489 in the thumb handle 441.

Operation and use of the hand-held surgical device 401 is very similar to that hereinbefore described in connection with the previous embodiments. A tool 491 of the type hereinbefore described can be inserted into the hand-held surgical device 401 in the manner hereinbefore described and is retained therein. As explained previously, the principal difference between hand-held surgical device 401 and the one previously described is that it utilizes a scissors-type grip rather than a pistol-type grip as disclosed in previous embodiments. This feature is advantageous to many surgeons because they are accustomed to utilizing scissors-type devices in surgery. This makes it possible for the surgeon to utilize the same type of action to which the surgeon is accustomed in performing surgical procedures. The hand-held surgical device 401 is also advantageous in that it can be utilized equally well by left-handed or right-handed surgeons because the controls are accessible from opposite sides and can be operated either by the left hand or the right hand, depending upon which hand the surgeon desires to use.

Another embodiment of a hand-held surgical device incorporating the present invention which is particularly adapted to be utilized by a surgical assistant is shown in FIGS. 38–42. The surgical device 501 consists of a housing 502 formed of two parts 502a and 502b and is generally in the form of a truncated cone. The housing 502 is provided with a finger recess 503 which is adapted to be engaged by a finger of the hand when the hand-held surgical device 501 is held by a human hand as hereinafter described.

An actuator tube assembly 506 is mounted for reciprocatory movement within the housing 502 similar to the actuator tube assembly hereinbefore described. It is provided with a bore 507 extending therethrough which is adapted to receive surgical tools of the type hereinbefore described. Handle or trigger means is provided for axially moving the actuator tube assembly 506 in the desired reciprocatory motion. The handle means consists of two parts which are adapted to be joined together in a suitable manner as for example by the use of push pins 512 extending into holes 513. The forward extremities of the handle parts 511a and 511b are provided with pivot holes 516 which are adapted to receive inwardly extending pins 517 provided on upwardly extending protrusions 518 formed as a part of the housing 502. The forward extremities of the handle parts 511a and 511b also carry downwardly extending protrusions 521 which are disposed between parallel spaced apart annular flanges 522 and 523 provided on the actuator tube assembly 506 for causing reciprocatory movement of the actuator tube assembly 506 as the handle 511 is pressed towards the housing 502.

This reciprocatory movement of the actuator tube assembly 506 in a proximal direction must be accomplished against the force of a coil spring 526 coaxially mounted on the actuator tube assembly 506. The coil spring 526 has one end engaging an annular flange 527 provided on the actuator tube assembly 506 and has the other end engaging inwardly extending arcuate protrusions 528 provided in the housing 502 (see FIG. 39). A cylindrical member 531 is threadedly mounted on the proximal extremity of the actuator tube assembly 506 by suitable means such as an adhesive (not shown). The cylindrical member 531 is provided with a hole 532 therein which opens into the bore 507 of the tube assembly 506 so that surgical tools of the type hereinbefore described can be inserted therethrough. The cylindrical member 531 is provided with longitudinally extending circumferentially spaced apart recesses 533 to aid in gripping the cylindrical member 531 by the fingers of the hand. Bayonet-type recesses 534 are provided on the exterior surface of the proximal extremity of the housing 502.

A nose cone 536 of the type hereinbefore described provided with circumferentially spaced protrusions 537 on the outer surface thereof is rotatably mounted on the housing 502 and is secured thereto to prevent longitudinal movement of the nose cone 536 with respect to the housing 502. The housing 502 is seated in an annular recess 538 provided in the nose cone 536 (see FIG. 40). Cooperative mating means is provided on the nose cone 536 and the actuator tube assembly 506 so that when the nose cone 536 is rotated by a finger of the hand, the actuator tube assembly 506 will be rotated while still permitting axial movement of the actuator tube assembly 506. Such cooperative mating means includes a pin 539 carried by the nose cone 536 and formed integral therewith which is disposed in an elongate recess 541 provided on the actuator tube assembly 506 and extending longitudinally thereof.

A ratchet pawl mechanism 551 is provided for retaining the actuator tube assembly 506 in a desired axial position as it is being advanced to actuate a tool carried by the device 501 as hereinafter described. This ratchet pawl mechanism 551 includes a knob or lever 552 mounted in the handle 511 extending upwardly out of the handle. This knob is adapted to assume three different positions as shown in FIGS. 43A, 43B and 43C. The first position shown in FIG. 43A is the "disengaged position" in which the ratchet knob 552 is proximal or to the rear in which the ratchet pawl mechanism 551 is deactivated permitting the trigger handle 511 to move unimpeded to any position. The second or midpoint position shown in FIG. 43B is the "passive" position in which the ratchet mechanism is passively engaged as hereinafter described. The third position is shown in FIG. 43C in which the ratchet knob is distal or forward and locks the ratchet mechanism.

The trigger knob or lever 552 is formed integral with a generally cylindrical body 553 which is disposed in a cylindrical recess 554 provided within the handle parts 511a and 511b and is pivotally mounted therein on a pin 556 supported by the handle parts 511a and 511b. The body 553 is arcuate in shape and is provided with a curved surface 557 which travels within the cylindrical recess 554. A rounded protrusion or detent 558 is provided on the outer surface and is adapted to engage a recess 559 formed in the handle or trigger 511. An arcuate slot 561 is formed in the body 553 and underlies the curved surface 557 to permit inward flexing of the portion of the body overlying the curved arcuate slot 561 so as to provide a spring member yieldably urging the detent 558 in an outward direction so it will be yieldably urged into the recess 559 when the lever or knob 552 is operated to move the detent 558 into registration with the recess 559. The body 553 is provided with a radially extending depending tab 563 which is adapted to engage a lip 564 carried by the upper extremity of a U-shaped pawl 566. The U-shaped pawl 566 is provided with first and second legs 567 and 568 which are generally spaced apart and parallel with a lateral extending portion 569 which carries the lip 564. Each of the legs 567 and 568 is provided with a hole 571 which is pivotally mounted on a pin 572 carried on the inner surface of a downwardly and proximally extending portion 573 of the handle 511.

A coil spring 576 (see FIG. 39) is provided and is mounted on the pin 553 and is seated within an arcuate recess 577 (see FIG. 42) provided in the body 553 and has one end 578 of the coil spring engaging a surface 579 provided in the body 553 and has the other end 581 extending through a small hole 582 provided in a transverse portion 569 of the pawl 566 and serves as an action spring as hereinafter described. Another coil spring 584 is provided which extends over the end 581 of the spring 576 and has one end engaging the top surface of the transverse portion 569 of the pawl 566 and has the other end engaging the coil spring 576. The spring 584 serves as a return spring. The legs 567 and 568 of the pawl 566 are provided with pawls 586 which are adapted to engage teeth 587 provided on inclined curved surfaces 588 of members 589 secured to the housing 502 by suitable means such as screws 591.

An audio feedback system is incorporated into the hand-held surgical device 501 and consists of longitudinally extending slots 593 which are provided on the actuator tube assembly 511 (see FIG. 39) immediately forward of the coil spring 526. The peaks and valleys formed by these longitudinally extending slots 593 on the actuator tube assembly 511 are engaged by a pin 594 yieldably urged in toward the actuator tube assembly 511. The pin 594 extends through a hole 596 provided in the member 589 carrying the teeth 587. The pin 594 is carried by flange sleeve 596 disposed on the other side of the member 589 which is slidably mounted on a protrusion 597 carried by the housing part 502a. A coil spring 598 is disposed on the sleeve and has one end engaging the flange portion as shown in FIG. 41 and has the other end engaging the inner surface of the body part 502a. With such a construction, it can be seen that as the actuator tube assembly 506 is rotated, click-click sounds will appear as the longitudinally extending slots are rotated past the pin or plunger 594 to audibly inform the surgeon of the rotation of the actuator tube assembly 506 and the speed of rotation by the rapidity at which the clicks are heard by the surgeon. The pin 594 also serves as a detent to yieldably retain the actuator tube assembly 506 in a desired position when the actuator tube assembly 506 is not being moved.

Operation and use of the hand-held surgical device 501 may now be briefly described as follows. Let it be assumed that a laparoscopic procedure is taking place and that the surgeon has an assistant who is utilizing the hand-held surgical device 501 shown in the drawings. Let it also be assumed by way of example that the surgical assistant wishes to utilize the hand-held device for use with a tool such as a grasper 599 having openable jaws 600. Let it be assumed that a gall bladder laparoscopic procedure is being performed and that it is desired to utilize the grasper 591 to pull up and expose the gall bladder so that it can be surgically removed by the surgeon performing the procedure. The assistant utilizes the hand-held surgical device 501 to introduce the grasper 591 through a trocar cannula (not shown) already introduced into the body of the patient. During the introduction, the handle 511 is engaged by the palm of the hand and the palm of the hand is utilized to hold the housing 502 which serves as a support for the grasper 599. The assistant compresses the handle 511 against the housing 502 to close the jaws 600 of the grasper 599 and introduces the grasper 599 into the body cavity of the patient into the vicinity of the gall bladder. The handle 511 can then be released to permit the actuator tube assembly 506 to move proximally under the force of the coil spring 526 to cause the jaws 600 of the grasper 599 to open. The grasper 599 then can be advanced over the gall bladder and the gall bladder clamped between the jaws 600 by using the fingers of the hand to press downwardly on the handle 511 to cause advancement of the actuator tube assembly 506 to cause closing of the jaws in the manner hereinbefore described in the previous embodiments.

Operation and use of the ratchet mechanism 551 provided in the hand-held surgical device 501 may now be briefly described in connection with the tasks being performed by the surgeon's assistant. As pointed out above, the ratchet knob or lever 552 is movable into three positions.

The surgeon's assistant during an initial introduction may wish to hold the ratchet knob 552 and may wish to bring back the ratchet knob to a proximal position so that the ratchet mechanism 551 is inoperative as shown in FIG. 43A. Thereafter let it be assumed that the grasper 599 has been moved into the vicinity of the gall bladder with the jaws 600 in an open position. After the jaws 600 have been moved onto the gall bladder, the assistant may move the ratchet knob 552 to an intermediate position to that shown in FIG. 43B in which the pawls 586 have been moved into engagement with the ratchet teeth 576 overcoming the force of the return spring 584 and moving the pawls 586 into engagement with the ratchet teeth 587. When this is the case, the handle 511 can be progressively pressed against the body 502 to cause the pawls 586 to progressively advance in the ratchet teeth and click by successive ratchet teeth to latch the handle 511 in the successive positions as it is advanced and as the jaws 600 are being closed on the gall bladder. If during this procedure it is desired to release the gall bladder and take another grasp, this can be readily accomplished merely by pressing on the lever 511 permitting the pawls 586 to disengage from the teeth and to permit the grasper to open under the force of the coil spring 526. Alternatively, the handle 511 can continue to be compressed until the gall bladder has been firmly grasped during which time the pawls 586 will progressively advance in the ratchet teeth 587 and be retained therein.

As soon as the assistant has ascertained that the jaws 600 have firmly grasped the gall bladder which can be ascertained by the surgeon's feel of the resistance provided by movement of the handle 511, the ratchet mechanism can be placed in a locked position by moving the ratchet knob 552 to the forwardmost or distal position shown in FIG. 43A so that the tab 563 carried by the body 553 engages the lip 564 and urges the pawls 586 into engagement with the ratchet teeth 587 to retain the same therein and to thereby lock the grasper onto the gall bladder. The surgeon's assistant can then release the handle 511 with the grasper having a firm grasp on the gall bladder.

It should be appreciated that in connection with the use of the hand-held surgical device 551, that the surgeon's assistant while utilizing the grasper 599 can rotate the grasper 599 if that is desired during the procedure. This can be readily accomplished while utilizing the index finger of the hand holding the device 501 to rotate the nose cone 536 in the desired direction. As this is being accomplished, audible sounds will be given out by the pin 594 engaging with the slots 593 carried by the actuator tube assembly 506. The pin 594 serves as a detent and retains the actuator tube in the desired position.

From the foregoing it can be seen that in the embodiment of the hand-held surgical device 501 hereinbefore described there has been provided a device which is relatively lightweight, simple and compact. It can be produced relatively inexpensively since a number of features provided on the hand-held surgical devices hereinbefore described have been eliminated and in particular the electrical functions, which have been eliminated. Even without these additional features, the hand-held surgical device has many desirable features. It is small and compact and can be readily used. It is particularly adapted for use with tools such as graspers which may require the use of a ratchet mechanism to aid in retaining the grasper in engagement with the tissue being engaged by the grasper.

Another hand-held surgical device 601 is shown in FIGS. 44–48 and incorporates another embodiment of the hand-held surgical device of the present invention. The device 601 is particularly adapted for use in gynecological surgical procedures where it is desired that the tools being utilized with the hand-held surgical device be utilized in a vertical orientation. The hand-held surgical device 601 for that reason has been provided with a vertical hand grip. The hand-held surgical device 601 consists of a housing 602 which is configured to fit in the palm of a human hand. Thus the housing 602 is provided with an indentation 603 which is adapted to receive the palm of the hand, the housing being formed so that the fingers can extend around the housing and extend through and into a large elongate hole 604 provided in a trigger handle 606. The handle is provided with a recess 607 which is adapted to receive the index finger of the hand. The housing 602 is provided with inclined outwardly extending surfaces 608 on opposite sides of the housing 602 which are provided with spaced apart parallel raised protrusions 609 which are adapted to be engaged by the thumb of the hand to provide a counterforce to the finger action on the trigger handle 606.

An actuator tube assembly 611 similar to that hereinbefore described is mounted for reciprocatory movement in the housing 602 in a vertical direction and is provided with a bore 610. The actuator tube assembly 611 includes a trombone-like connection hereinbefore described for the previous embodiments. Means is provided for causing reciprocatory movement of the actuator tube assembly 611 and consists of a yoke 612 which is pivotally mounted on a pin 613 carried by the housing 602 (see FIG. 45). The distal extremity of the yoke 612 is pivotally connected by a pin 614 to the trigger handle 606. The proximal extremities of the Y-shaped yoke 612 is rounded as shown in FIG. 45 and is disposed between first and second annular flanges 616 and 617 provided on the actuator tube assembly 611.

The trigger handle 606 is mounted for movement in an elongate slot 618 provided in the housing 602 for movement into and out of the housing. This is accomplished by utilizing an idler arm 619 which has one end pivotally connected to the trigger handle 606 by a pin 621 and which has the other end secured to the housing 602 by a pin 623. The idler arm 619 is disposed generally parallel to the yoke 613 to in effect provide a parallelogram-type motion for the trigger handle 606. Spring means in the form of U-shaped spring 621 is provided within the housing 602 for yieldably urging the trigger handle 606 into an outermost position through the slot 618 as determined when the actuator tube assembly 611 is in its proximal most or rearmost position within the housing 602. One end of the U-shaped spring 621 engages a pin 622 in the housing 602 and the other end engages the pin 614 carried by the trigger handle 606.

Because of the vertical orientation of the hand-held surgical device 601 it is necessary to provide means for rotating the actuator tube assembly 611 which is accessible to the fingers of the hand holding the hand-held surgical device 601. As shown particularly in FIGS. 45 and 46, a right angle transfer rotation mechanism is provided which takes the form of a thumb wheel 626 which is accessible through slots 627 provided on opposite sides of the housing 602. Thumb wheel 626 is provided with recesses 628 spaced apart circumferentially of the thumb wheel 626 which is adapted to be readily engaged by the thumb. The thumb wheel 626 is also provided with axially disposed cylindrical protrusions 629 for rotatably mounting the thumb wheel 626 in the structure of the housing. As shown, the thumb wheel 626 is mounted so that it is disposed in one side of the actuator tube assembly 611. Thumb wheel 626 is provided with additional cylindrical protrusions 631 which are spaced apart circumferentially and extend at right angles to the recesses 628. Protrusions 631 are adapted to mate with a gear 632 which is provided with longitudinally and axially extending slots spaced circumferentially around the gear 632. The gear 632 is affixed to the actuator tube assembly 611 and can be formed integral therewith. Thus it can be seen that as the thumb wheel 626 is rotated by the thumb of the hand holding the device 601. The rotary motion of the thumb wheel 626 is translated into rotary motion of the gear 632 in a direction which is at right angles to the rotation of the thumb wheel 626.

A ratchet mechanism 641 is provided in the housing which consists of a U-shaped pawl member mounted within the housing. The U-shaped pawl member 642 is provided with legs 643 and 644 which carry pawls 646 (see FIG. 45) which are adapted to engage teeth 647 by two spaced-apart portions 606a and 606b of the trigger handle 606 (see FIGS. 45 and 47). A U-shaped pawl 642 is provided with cylindrical protrusions 651 which extend through the housing 602 and are connected to knobs 652 provided on opposite sides of the housing 602. The knobs 652 are provided with outwardly projecting protrusions 653 adapting the knobs to be engaged by the thumb of the hand holding the device 601. The knobs 652 are operable to swing the pawls 646 into engagement with the teeth 647. By swinging movement of the knobs 652 which are movable in the direction indicated by the arrow 654 (see FIG. 44) the knobs 652 are moved into and out of recesses 656 formed in the outer surface of the housing 602.

As described with the previous embodiment of the hand-held surgical device shown in FIG. 31, the device is provided with cut and coag push buttons 661 and 662 which are adapted to be engaged by the index finger of the hand engaging the handle. It is also provided with a rocker arm 666 mounted on the housing 602 which is adapted to be engaged by the thumb of the hand for movement between the two positions for operating two switches (not shown) for performing suction and liquid delivery as hereinbefore described. These switches 661, 662 and 666 are connected to electrical circuitry of the type described in co-pending application Ser. No. 08/128,309, filed Sep. 28, 1993, now U.S. Pat. No. 5,512,721 now U.S. Pat. No. 5,141,498, and are connected to a flex circuit which in turn is mounted within the housing (not shown) and connected to a cable 671. A nut 676 of the type hereinbefore described is mounted on the actuator tube assembly 611. A bayonet-type recess 677 for mating with surgical tools as hereinbefore described is provided on the housing 602.

An outer tubular member 681 formed of a suitable material such as plastic is secured to a nose cone 682. The nose cone 682 is secured to the housing 602 in a suitable manner such as a threaded connection (not shown). It carries a cylindrical tube 686 which is slidably mounted over a metal tube 687 mounted on the distal extremity of the actuator tube assembly 611 to provide a trombone-like slide connection hereinbefore described.

Spring means is provided for yieldably disengaging and returning the pawl 642 and for yieldably returning the knobs 652 into positions so they are disposed within the recesses 656 provided in the housing 602. The spring means consists of a coil spring 657 which is mounted on the pin 621 and has one end 658 engaging a protrusion 642a and has the other end 659 engaging the housing 602.

Means is provided for giving an audible indication of the rotation of the thumb wheel 626 and consists of a U-shaped spring member 634 (see FIGS. 45 and 46). One end of the spring member 634 is provided with a vee-shaped detent 636 which is adapted to engage vee-shaped recesses spaced circumferentially apart on the thumb wheel 626 opposite the protrusions 631. The other end of the U-shaped spring member 636 is suitably retained in the housing as for example by mounting the same on rib portions 638 carried by the housing 602. In this way it can be seen that as the thumb wheel 626 is advanced, a click sound will be given by the advancement of the vee-shaped detent 636 into and out of the recesses 637 as the recesses are advanced past the detent 636 to thus give the surgeon utilizing the device an audible indication of the amount of rotation and to stabilize the rotary position.

From the foregoing it can be seen that there has been provided a hand-held surgical device of various configurations which all utilize a tool actuator tube assembly. Each configuration has advantages as hereinbefore described.

What is claimed is:

1. A hand-held surgical device for use with a human hand in performing a laparoscopic medical procedure and for use with a plurality of tools comprising a housing, a non-removable actuator tube assembly slidably mounted in the housing and handle means carried by the housing adapted to be grasped and held by the human hand and having means adapted to be engaged by the fingers of the human hand for causing reciprocatory movement of the actuator tube assembly within the housing, said actuator tube assembly having a bore extending axially therethrough and being sized to receive said plurality of tools one at a time and having means adapted to engage a tool inserted into the bore to cause operation of the tool when said actuator tube assembly is reciprocated.

2. A hand-held surgical device for use with a human hand having a palm, four fingers and a thumb in performing a laparoscopic medical procedure comprising a housing, a non-removable actuator tube assembly slidably mounted in the housing and handle means carried by the housing, said handle means including a pistol grip adapted to be engaged by the palm and the four fingers of the hand and a scissors-type pivotally mounted looped handle movable toward and away from the pistol grip and adapted to be engaged by the thumb of the same hand and means coupled to the looped handle for causing reciprocatory movement of the actuator tube assembly as the looped handle is moved.

3. A hand-held surgical assembly for use in performing a laparoscopic medical procedure comprising a housing, a non-removable actuator tube assembly slidably mounted in the housing and handle means carried by the housing and means carried by the handle means for causing reciprocatory movement of the actuator tube assembly within the housing, said actuator tube assembly having a bore extending axially therethrough, a ratchet mechanism disposed within the housing cooperatively associated with the actuator tube assembly so that the actuator tube assembly can be retained in a predetermined position as the actuator tube assembly is reciprocated in a distal direction and operable tool means removably mounted in said bore of said actuator tube assembly and having a proximal portion thereof extending out of the actuator tube permitting the same to be grasped by the hand to aid in insertion and removal of the operable tool means from the actuator tube assembly.

4. A device as in claim 3 wherein said ratchet mechanism includes a pawl and ratchet teeth and in which the pawl is adapted to engage the ratchet teeth together with spring means yieldably urging the pawl out of engagement with the ratchet teeth.

5. A device as in claim 3 together with control means disposed on each of opposite sides of the housing adapted to cause actuation of the ratchet mechanism so that the device is ambidextrous for operation by the right hand or the left hand holding the device.

6. A device as in claim 5 together with means for causing rotation of the actuator tube assembly, said means for causing rotation of the actuator tube assembly being accessible from either of opposite sides of the housing and being in close proximity to the control means for causing actuation of the ratchet mechanism.

7. A hand-held surgical assembly for use in performing a laparoscopic medical procedure comprising a housing, an actuator tube having a bore therein slidably mounted in the housing and a handle operated means carried by the housing for causing reciprocatory movement of the actuator tube assembly within the housing, a ratchet mechanism disposed within the housing and being cooperatively associated with the actuator tube assembly so that the actuator tube assembly can be retained in a predetermined position as the actuator tube assembly is reciprocated in a distal direction and means mounted on the housing and engaging the actuator tube assembly for rotating the actuator tube assembly and detent means mounted in the housing and engaging the actuator tube assembly for yieldably retaining the actuator tube assembly in a predetermined rotational position.

8. A device as in claim 7 wherein said detent means is formed to provide an audible sound as the actuator tube is rotated.

9. A device as in claim 8 wherein said ratchet mechanism includes a ratchet knob movable to cause said ratchet mechanism to move between three positions, the first position retaining the pawl out of engagement with the ratchet teeth, the second position permitting the pawl to engage the ratchet teeth but permitting the pawl to be released under the force of the spring when the pawl is frictionally released from the ratchet teeth, and a third position in which the pawl is retained in engagement with the ratchet teeth.

10. A hand-held surgical device for use with a human hand having fingers in performing a function in a laparoscopic medical procedure by use of a human hand of a person comprising a housing having opposite sides, a non-removable actuator tube assembly slidably mounted in the housing and handle means carried by the housing adapted to be engaged and grasped by the human hand, means carried by the handle means for causing reciprocatory movement of the actuator tube assembly within the housing, at least one electrical switch for controlling said function mounted on each of opposite sides of the housing for performing said function and adapted to be engaged by a finger of the hand engaging the handle means so that the device can be operated either by the right hand or the left hand of the person holding the device.

11. A hand-held surgical device for use in performing first and second functions in a laparoscopic medical procedure by use of a human hand of a person comprising a housing having opposite sides, an actuator tube assembly having a bore therein slidably mounted in the housing and hand operated means carried by the housing engageable by the hand of the person for causing reciprocatory movement of the actuator tube assembly within the housing, first and second electrical switches mounted on opposite sides of the housing for controlling said first and second functions and adapted to be engaged by a finger of the hand so that the device can be operated either by the right hand or the left hand of the person holding the device and additional electrical switch means carried by the housing for controlling in a single location the first and second functions and being centered so that the additional switch means can be operated by a finger of a right or a left hand holding the device.

12. A device as in claim 11 for performing two additional functions and wherein said additional switch means is in the form of a rocker switch capable of controlling the two functions with only one additional function being selectable at a time.

13. A reusable hand-held surgical assembly for use in performing a laparoscopic medical procedure by use of a human hand having fingers comprising a housing, an actuator tube assembly having a bore therein slidably mounted in the housing, a hand grip secured to the housing and adapted to be grasped by the human hand, said hand grip including means for causing reciprocatory movement of the actuator tube assembly within the housing, operable tool means removably mounted in said bore, said operable tool means including tool parts and an actuation mechanism cooperating with the actuator tube for causing operation of the tool parts as the actuator tube is reciprocated, means for establishing a substantially fluid-tight seal in the bore between the actuator tube and the operable tool means, means connected to the housing for supplying an irrigation liquid and suction to the operable tool means for performing irrigation and suction functions and means secured to the housing for supplying electrical energy to the operable tool means for performing an electro-cautery function and switch means carried by the housing and accessible by the fingers of the hand holding the hand grip for selecting electro-cautery, irrigation and suction functions.

14. An assembly as in claim 13 wherein said switch means carried by the housing is positioned on the housing so that it can be operated by the fingers of a left hand or a right hand of a human being.

15. An assembly as in claim 14 wherein said switch means includes at least one rocker switch movable between first and second positions for controlling at least two of the electro-cautery, irrigation and suction functions.

16. A reusable hand-held surgical device for use in performing a laparoscopic medical procedure by the use of a human hand having fingers and for use with a tool comprising a housing, a tube having a bore therein mounted in the housing and adapted to receive said tool, a hand grip secured to the housing and adapted to be grasped by the human hand, sealing means carried within the bore in said tube being adapted to form a substantially fluid-tight seal between the tube and a tool when the tool is inserted into the bore therein, means connected to the housing for supplying an irrigation liquid into the bore in the tube for performing an irrigation function, means connected to the housing for supplying suction to the tube to provide a suction function and means secured to the housing for supplying electrical energy to a tool provided in the bore for providing an electro-cautery function and switch means carried by the housing and accessible by the fingers of the hand holding the hand grip for selecting irrigation, suction and electro-cautery functions.

17. A device as in claim 16 wherein said tube serves as an actuator tube and is slidably mounted in the housing and wherein the hand grip means includes means for causing reciprocatory movement of the tube within the housing.

\* \* \* \* \*